United States Patent
Fox et al.

(10) Patent No.: US 6,417,194 B1
(45) Date of Patent: *Jul. 9, 2002

(54) QUINOLINES AND QUINAZOLINES USEFUL IN THERAPY

(75) Inventors: David Nathan Abraham Fox, Sandwich; Alan John Collis, Romford; Simon John Mantell, Sandwich, all of (GB)

(73) Assignee: Pfizer, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/499,623

(22) Filed: Feb. 7, 2000

Related U.S. Application Data

(62) Division of application No. 09/067,588, filed on Apr. 28, 1998.

(30) Foreign Application Priority Data

Jun. 5, 1997 (GB) .............................................. 9711650

(51) Int. Cl.[7] ...................... A61K 31/47; A61K 31/505; C07D 239/02; C07D 239/72; C07D 217/00
(52) U.S. Cl. ........................ 514/307; 514/259; 544/297; 544/283; 544/291; 546/139; 546/259
(58) Field of Search ................................ 514/307, 259; 544/283, 291, 297; 546/139, 259

(56) References Cited

U.S. PATENT DOCUMENTS 6,015,819 A * 1/2000 Gluchowski et al. ....... 544/283
6,048,864 A * 4/2000 Abraham et al. ........... 514/260

FOREIGN PATENT DOCUMENTS

EP      799619      * 10/1997

OTHER PUBLICATIONS

Cockrum, Paul C. et al. "A Pharm. analysis of patients with sym.BPH", Pharmco. 11/6.550–65, Jun. 1997.*

* cited by examiner

Primary Examiner—Mukund J. Shah
Assistant Examiner—Sudhaker B. Patel
(74) Attorney, Agent, or Firm—Peter C. Richardson; Paul H. Ginsburg

(57) ABSTRACT

Compounds of formula I, wherein
$R^1$ represents $C_{1-4}$ alkoxy optionally substituted by one or more fluorine atoms;
$R^2$ and $R^3$ independently represent H or $C_{1-6}$ alkoxy (which is optionally substituted);
$R^4$ represents a 4-, 5-, 6- or 7-membered heterocyclic ring, the ring being optionally fused to a benzene ring or a 5- or 6-membered heterocyclic, the ring system as a whole being optionally substituted;
X represents CH or N; and
L is absent,
or represents a cyclic group of formula Ia, or represents a chain of formula Ib, and pharmaceutically acceptable salts thereof; are useful in therapy, in particular in the treatment of benign prostatic hyperplasia.

7 Claims, No Drawings

QUINOLINES AND QUINAZOLINES USEFUL IN THERAPY

This application is a divisional of U.S. patent application Ser. No. 09/067,588, filed Apr. 28, 1998, allowed Nov. 9, 1999, which claims priority from GB Application No. 9711650.3, filed Jun. 5, 1997.

This invention relates to novel compounds useful in therapy, particularly in the treatment of benign prostatic hyperplasia.

International Patent Application WO 89/05297 discloses a number of substituted quinazoline compounds that are indicated as inhibitors of gastric acid secretion.

Co-pending International Patent Application No. PCT/EP96/05609 discloses a number of quinoline and quinazoline compounds indicated in the treatment of benign prostatic hyperplasia, and discloses 4-amino-6-benzyloxy-7-methoxy-2-[4-(4-morpholinecarbonyl)-1,4-diazepan-1-yl] quinazoline as an intermediate [see Example 49, step (f), therein]. This is the compound of Example 1 of the present application, which is excluded from claim 1 by proviso (b).

According to the present invention, there is provided a compound of formula I, wherein
$R^1$ represents $C_{1-4}$ alkoxy optionally substituted by one or more fluorine atoms;
$R^2$ and $R^3$ independently represent H, $C_{1-6}$ alkoxy (optionally substituted by one or more fluorine atoms, or by phenyl which may in turn be substituted by one or more fluorine atoms), cyclobutyloxy or $CF_3CH_2O$.
$R^4$ represents a 4-, 5-, 6- or 7-membered heterocyclic ring containing at least one heteroatom selected from N, O and S, the ring being optionally fused to a benzene ring or a 5- or 6-membered heterocyclic ring containing at least one heteroatom selected from N, O and S, the ring system as a whole being optionally substituted by one or more groups independently selected from OH, $C_{1-4}$ alkyl, $C_{1-4}$ alkoxy, halogen and $NHSO_2(C_{1-4}$ alkyl), and when S is a member of the ring system, it may be substituted by one or two oxygen atoms;
X represents CH or N; and
L is absent,
or represents a cyclic group of formula Ia, in which A is attached to $R^4$;
A represents CO or $SO_2$,
Z represents CH or N;
m represents 1 or 2, and in addition, when Z represents CH, it may represent 0; and
n represents 1, 2 or 3, provided that the sum of m and n is 2, 3, 4 or 5;

or represents a chain of formula Ib, in which A is attached to $R^4$;
A and Z are as defined above;
$R^5$ and $R^6$ independently represent H or $C_{1-4}$ alkyl; and
p represents 1, 2 or 3, and in addition, when Z represents CH, it may represent 0;
provided that:
(a) $R^2$ and $R^3$ do not both represent H;
(b) when $R^1$ represents methoxy, $R^2$ represents benzyloxy, $R^3$ represents H, $R^4$ represents morpholinyl, and X represents N, then L is not ; and (c) when X represents N and L is absent, then $R^4$ is not naphthyridine;
or a pharmaceutically acceptable salt thereof (referred to together herein as "the compounds of the invention").

Alkyl groups may be straight chain, branched, cyclic or a combination thereof. Similarly, the alkyl portion of alkoxy groups may be straight chain, branched, cyclic or a combination thereof.

Preferably, heterocyclic rings represented or comprised by $R^4$ are saturated. Examples include morpholine, tetrahydrofuran and piperidine.

The compounds of the invention may be optically active. The invention includes all optical isomers of the compounds of formula I, and all diastereoisomers thereof.

Preferred groups of compounds that may be mentioned include those in which:
(a) $R^1$ represents methoxy;
(b) $R^2$ represents H or methoxy;
(c) $R^3$ represents cyclobutyloxy or $CF_3CH_2O$;
(d) L is absent, in which case $R^4$ preferably represents a piperidine ring which is fused to a pyridine ring or to a benzene ring which is substituted by $NHSO_2(C_{1-4}$ alkyl); and
(e) L represents

, in which case $R^4$ preferably represents morpholinyl.
When $R^3$ represents H, $R^2$ is preferably benzyloxy or cyclobutyloxy.

According to the invention, there is also provided a process for the production of a compound of the invention, which comprises:
(a) when X represents CH, cyclizing a compound of formula II,

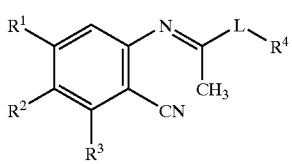

II

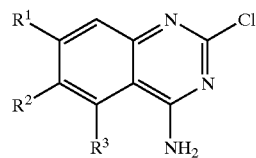

VII in which $R^{1-4}$ and L are as defined above;

(b) when Z represents N, and L is present, reacting a compound of formula IIIa or IIIb, as appropriate,

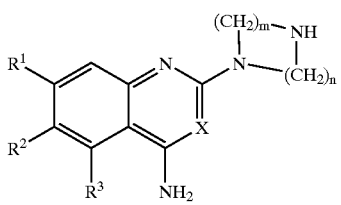

IIIa

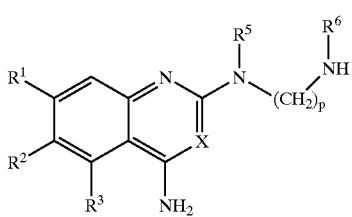

IIIb in which $R^1$, $R^2$, $R^3$, $R^5$, $R^6$, X, m, n and p are as defined above, with a compound of formula IV, Lg—A—$R^4$      IV in which $R^4$ and A are as defined above, and Lg represents a leaving group;

(c) reacting a compound of formula V,

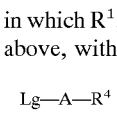

V in which $R^1$, $R^4$, X and L are as defined above, and $R^a$ and $R^b$ independently represent H or OH, provided that they do not both represent H, with a compound of formula VI, $R^c$—Lg      VI in which $R^c$ is alkyl (optionally substituted by one or more fluorine atoms, or by pheny which may in turn be substituted by one or more fluorine atoms), and Lg represents a leaving group, in the presence of a base;

(d) when X represents N, reacting a compound of formula VII, in which $R^1$, $R^2$ and $R^3$ are as defined above, with a compound of formula VIIIa, VIIIb or VIIIc, as appropriate,

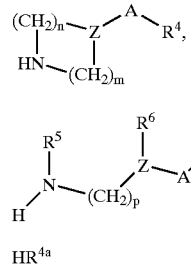

VIIIa

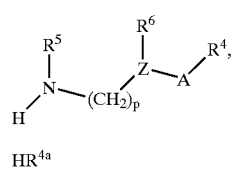

VIIIb

H$R^{4a}$      VIIIc in which $R^{4-6}$, A, Z, m, n and p are as defined above; and $R^{4a}$ has the same significance as $R^4$ above except that it contains a nucleophilic nitrogen atom in the heterocyclic ring which is attached to the H in formula VIIIc;

(e) when A represents CO and $R^4$ comprises a nucleophilic nitrogen atom in the heterocyclic ring attached to L, reacting a compound of formula IXa or IXb, as appropriate,

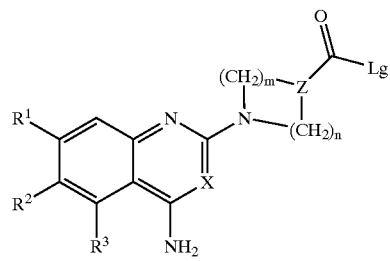

IXa

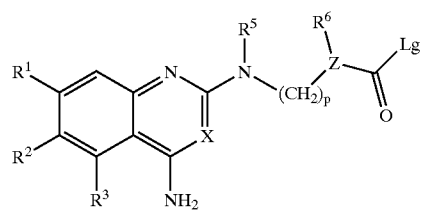

IXb in which $R^{1-3}$, $R^5$, $R^6$, X, Z, m, n and p are as defined above, and Lg is a leaving group, with a compound of formula VIIIc, as defined above; or (f) conversion of a compound of formula I in which L represents a cyclic group of formula Ia, to a corresponding compound of formula I in which L represents a chain of formula Ib in which $R^5$ and $R^6$ each represent H, by the action of a strong base; and where desired or necessary converting the resulting compound of formula I into a pharmaceutically acceptable salt or vice versa.

In process (a), the cyclization may be carried out in the presence of a strong base (for example lithium diisopropylamide) in a solvent that does not adversely affect the reaction (for example tetrahydrofuran), around room temperature. Alternatively, it may be performed using potassium hydroxide or potassium tert-butoxide in a solvent which does not adversely affect the reaction (for example dimethylsulphoxide or 1,2-dimethoxyethane), at an elevated temperature (for example 80θC). In addition, it may be performed using zinc chloride either without a solvent at an elevated temperature (for example 190θC), or in a solvent which does not adversely affect the reaction (for example dimethylformamide at the reflux temperature of the solvent).

In process (b), suitable leaving groups are OH and Cl. When the compound of formula IV is a carboxylic acid, the reaction may be carried out in the presence of conventional coupling agents [for example 1-hydroxybenzotriazole monohydrate, 1-(3-dimethylaminopropyl)-3-ethylcarbodiimide hydrochloride and 4-methylmorpholine] in a solvent which does not adversely affect the reaction (for example $CH_2Cl_2$) at or around room temperature. When the leaving group is Cl, the reaction may be carried out in a solvent which does not adversely affect the reaction (for example $CH_2Cl_2$ or tetrahydrofuran), around 0θC or up to the reflux temperature of the solvent.

In process (c), suitable leaving groups include halogens such as bromine or iodine, and suitable bases include sodium hydride. The reaction may be carried out in a solvent that does not adversely affect the reaction (for example dimethylformamide) at room temperature or up to the reflux temperature of the solvent.

In process (d), the reaction may be carried out in a solvent which does not adversely affect the reaction (for example n-butanol) in the presence of a base (for example triethylamine) at an elevated temperature (for example the reflux temperature of the solvent).

In process (e), suitable leaving groups include Cl. The reaction may be carried out in a solvent that does not adversely affect the reaction (for example THF) in the presence of a base (for example triethylamine) at room temperature.

The reaction may also be carried out without isolating the compound of formula IXa or IXb, by reacting a compound of formula IIIa or IIIb with triphosgene and a compound of formula VIIIc. In this case the leaving group is —Cl. The reaction may be carried out in a solvent that does not adversely affect the reaction (for example $CH_2Cl_2$) in the presence of a base (for example triethylamine) at or around room temperature.

In process (f), suitable strong bases include lithium diisopropylamide. The reaction may be carried out in a solvent that does not adversely affect the reaction (for example THF).

Compounds of formula II [see process (a)] may be prepared by reaction of a compound of formula X,

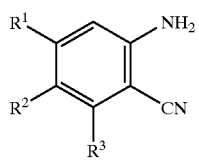

X in which $R^1$, $R^2$ and $R^3$ are as defined above, with a combination of a compound of formula XI,

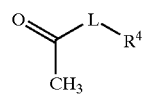

XI in which $R^4$ and L are as defined above, and phosphorous oxychloride in dichloromethane at the reflux temperature of the solvent.

Compounds of formula X may be prepared from compounds of formula XII,

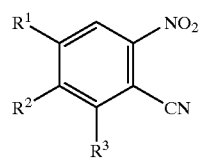

XII in which $R^{1-3}$ are as defined above, by reaction with $Na_2S_2O_4$. The reaction may be carried out in a vigorously stirred mixture of dichloromethane and water, at room temperature.

Compounds of formula XII may be prepared from compounds of formula XIII,

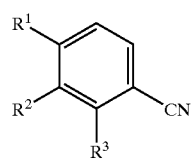

XIII in which $R^{1-3}$ are as defined above, by reaction with $NO_2BF_4$. The reaction may be carried out in acetonitrile at around 0θC.

Alternatively, compounds of formula X may be prepared from compounds of formula XIV,

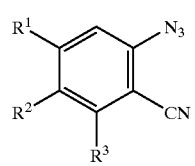

XIV in which $R^{1-3}$ are as defined above, by reaction with (a) magnesium turnings in methanol at room temperature; or (b) triphenylphosphine in tetrahydrofuran at room temperature in the presence of water to form a phosphonimide, followed by acidic hydrolysis.

Compounds of formula XIV may be prepared from compounds of formula XV,

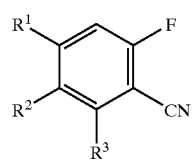

XV in which $R^{1-3}$ are as defined above, by reaction with sodium azide in dimethylformamide, at an elevated temperature (for example 115θC).

Compounds of formula IIIa or IIIb [see process (b)] in which X represents CH may be prepared from compounds of formula XVIa or XVIb, as appropriate,

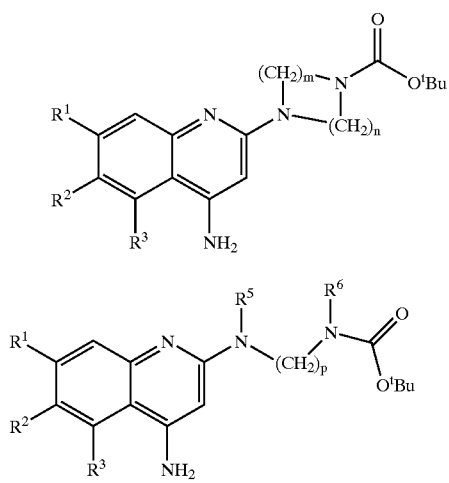

XVIa

XVIb in which $R^{1-3}$, $R^5$, $R^6$, m, n and p are as defined above, by bubbling HCl gas through a solution of the compound in dichloromethane.

Compounds of formula XVIa or XVIb may be prepared from compounds of formula XVIIa or XVIIb, as appropriate,

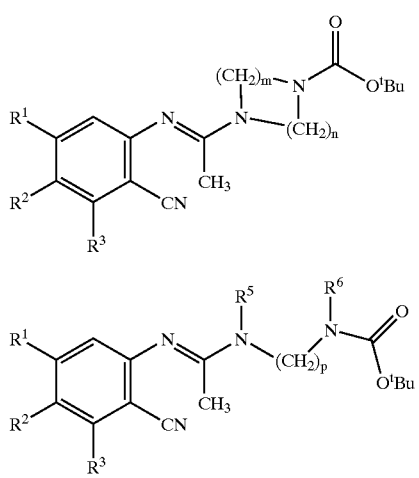

XVIIa

XVIIb in which $R^{1-3}$, $R^5$, $R^6$, m, n and p are as defined above, by cyclization using potassium hydroxide at an elevated temperature (such as 90°C) in DMSO, quenching with water, or lithium diisopropylamide at room temperature in THF, quenching with water.

Compounds of formula XVIIa or XVIIb may be prepared by reacting a compound of formula X, as defined above, with a compound of formula XVIIIa or XVIIIb, as appropriate,

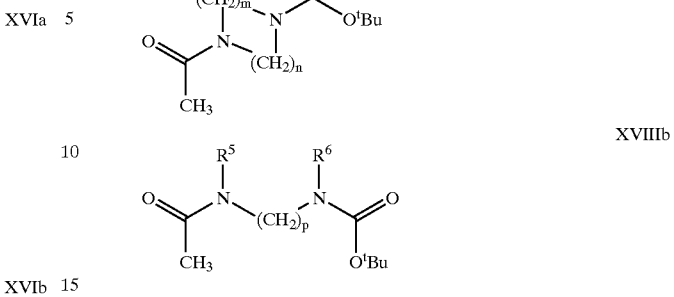

XVIIIa

XVIIIb in which $R^5$, $R^6$, m, n and p are as defined above, by the method described above for producing compounds of formula II.

Compounds of formula IIIa or IIIb [(see process (b)] in which X represents N may be prepared by reacting a compound of formula VII, as defined above, with a compound of formula XIXa or XIXb, as appropriate,

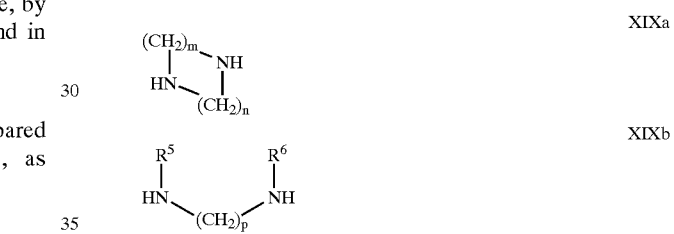

XIXa

XIXb in which $R^5$, $R^6$, m, n and p are as defined above, using the conditions mentioned for process (d) above.

Compounds of formula VII may be prepared by conventional means from known compounds (or compounds available using known techniques) according to Scheme 1 below (see also Examples 8 and 9), in which $R^{1-3}$ are as defined above:

Scheme 1

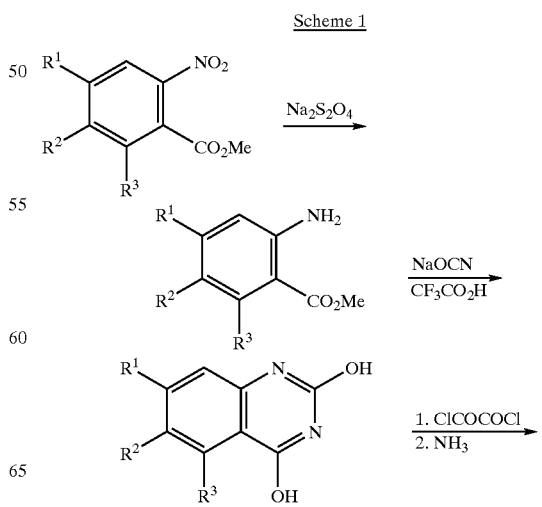

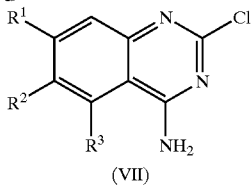

(VII)

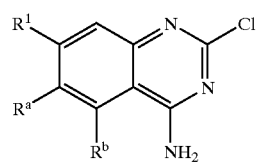

XXI

Compounds of formula V [see process (c)] in which X represents CH may be prepared by cyclization of a compound of formula XX,

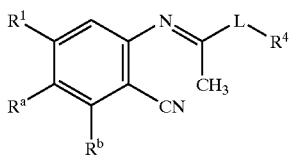

XX in which $R^1$, $R^4$, $R^a$, $R^b$ and L are as defined above, using the reaction conditions mentioned in process (a) above.

Compounds of formula XX may be prepared by conventional means from known compounds (or compounds available using known techniques) according to Scheme 2 below [see also Example 1(a)–(c) and Example 6(a)], in which $R^1$, $R^4$, $R^a$, $R^b$ and L are as defined above:

Scheme 2

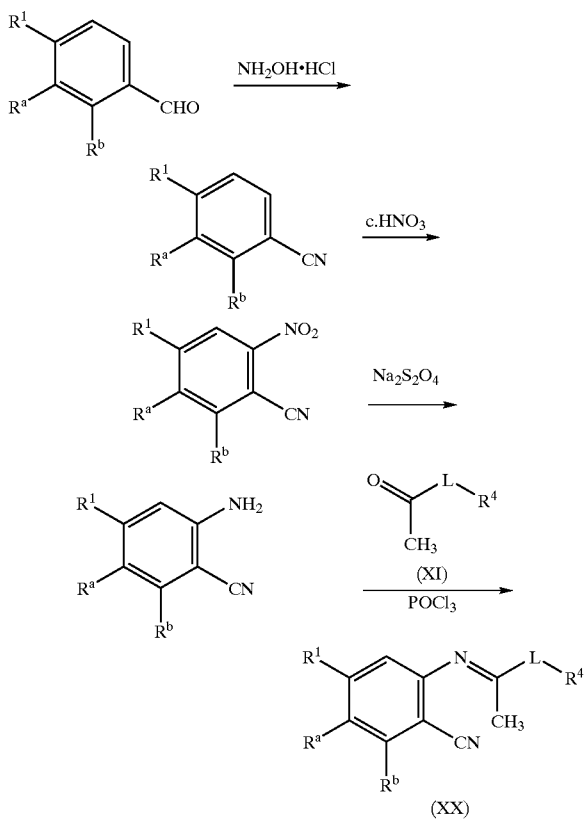

Compounds of formula V in which X represents N may be prepared from compounds of formula XXI, in which $R^1$, $R^a$ and $R^b$ are as defined above, by reaction with a compound of formula VIIIa, VIIIb or VIIIc, as defined above, as appropriate, using the conditions described in process (d).

Compounds of formula XXI may be prepared by methods analogous to those set out in scheme 1 above for the preparation of compounds of formula VII.

The preparation of compounds of formula VII [see process (d)] has already been described above.

Compounds of formula VIIIa and VIIIb may be prepared by reaction of a compound of formula IV, as defined above, with a compound of formula XIXa or XIXb, as defined above, as appropriate, using the conditions indicated for process (d) above.

Compounds of formula IXa and IXb [see process (e)] in which Lg represents Cl may be prepared from compounds of formula IIIa or IIIb, as defined above, as appropriate, by reaction with triphosgene. The reaction may be carried out in a solvent which does not adversely affect the reaction (for example $CH_2Cl_2$) in the presence of a base (for example triethylamine) at around $-10\theta C$.

Compounds of formulae IV, VI, VIIIc, XI, XIII, XV, XVIIa, XVIIb, XIXa and XIXb are either known or are available using known techniques.

The intermediate compounds of formulae II, IIIa, IIIb, V, VII, IXa and IXb form a further aspect of the invention.

It will be apparent to those skilled in the art that sensitive functional groups may need to be protected and deprotected during synthesis of a compound of the invention. This may be achieved by conventional techniques, for example as described in 'Protective Groups in Organic Synthesis' by T W Greene and P G M Wuts, John Wiley and Sons Inc, 1991.

The compounds of the invention are useful because they possess pharmacological activity in animals. In particular, the compounds are useful in the treatment of a number of conditions including hypertension, myocardial infarction, male erectile dysfunction, hyperlipidaemia, cardiac arrhythmia and benign prostatic hyperplasia. The latter condition is of particular interest. Thus, according to another aspect of the invention, there is provided a method of treatment of benign prostatic hyperplasia which comprises administering a therapeutically effective amount of a compound of the invention to a patient suffering from such a disorder. The use of the compounds of the invention as pharmaceuticals, and the use of the compounds of the invention in the manufacture of a medicament for the treatment of benign prostatic hyperplasia, are also provided.

The compounds of the invention may be administered by any convenient route, for example orally, parenterally (e.g. intravenously, transdermally) or rectally. The daily dose required will of course vary with the particular compound used, the particular condition being treated and with the severity of that condition. However, in general a total daily dose of from about 0.01 to 10 mg/kg of body weight, and preferably about 0.05 to 1 mg/kg, is suitable, administered from 1 to 4 times a day.

The compounds of the invention will generally be administered in the form of a suitable pharmaceutical formulation.

Thus, according to another aspect of the invention, there is provided a pharmaceutical formulation including preferably less than 50% by weight of a compound of the invention in admixture with a pharmaceutically acceptable adjuvant, diluent or carrier. The pharmaceutical formulation is preferably in unit dose form. Such forms include solid dosage forms, for example tablets, pills, capsules, powders, granules, and suppositories for oral, parenteral or rectal administration; and liquid dosage forms, for example sterile parenteral solutions or suspensions, suitably flavoured syrups, flavoured emulsions with edible oils such as cottonseed oil, sesame oil, coconut oil and peanut oil, and elixirs and similar pharmaceutical vehicles.

Solid formulations may be prepared by mixing the active ingredient with pharmaceutical carriers, for example conventional tabletting ingredients such as corn starch, lactose, sucrose, sorbitol, talc, stearic acid, magnesium stearate, dicalcium phosphate, gums and other diluents, for example water, to form a homogeneous preformulation formulation in which the active ingredient is uniformly dispersed so that it may be readily subdivided into equally effective unit dosage forms containing typically from 0.1 to about 500 mg of the active ingredient. The solid dosage forms may be coated or otherwise compounded to prolong the action of the formulation.

The formulations of the invention may also contain a human 5-$\Delta$ reductase inhibitory compound [see International Patent Application WO 95/28397], or a compound of the invention could be presented in a pharmaceutical pack also containing a human 5-$\Delta$ reductase inhibitory compound as a combined preparation for simultaneous, separate or sequential use.

The compounds of the invention may be tested in the screens set out below.

Contractile Responses of Human Prostate

Prostatic tissue was cut into longitudinal strips (approximately 3×2×10 mm) and suspended in organ baths under a resting tension of 1 g in Krebs Ringer bicarbonate of the following composition (mM): NaCl (119), KCl (4.7), CaCl$_2$ (2.5), KH$_2$PO$_4$ (1.2), MgSO$_4$ (1.2), NaHCO$_3$ (25), glucose (11), and gassed with 95% O$_2$/5% CO$_2$.

The solution also contained 10 mM cocaine and 10 mM corticosterone. Tissues were exposed to a sensitising dose of (−)-noradrenaline (100 mM) and washed over a 45 minute period. Isometric contractions were obtained in response to cumulative additions of (−)-noradrenaline to obtain control curves in all tissues. A further curve was then generated in the presence or absence of antagonist (incubated for 2 hours). Antagonist affinity estimates (pA$_2$) were determined using a single concentration of competing antagonist, pA$_2$=−log [A]/(DR-1) where the dose ratio (DR), relative to corresponding controls, was produced by a single concentration of antagonist [A], assuming competitive antagonism and Schild regression close to unity.

Anaesthetised Dog Model of Prostatic Pressure and Blood Pressure

Mature male beagles (12–15 kg body weight) were anaesthetised with sodium pentobarbitone (30–50 mg/kg i.v.) and a tracheal cannula was inserted. Subsequent anaesthesia was maintained using pentobarbitone infusion. The animals were respirated with air using a Bird Mk8 respirator (Bird Corp., Palm Springs, Calif., USA) adjusted to maintain blood gasses in the range pO$_2$ 90–110 mm Hg, pCO$_2$ 35–45 mm Hg, pH 7.35–7.45. Body temperature was maintained at 36–37.5θC using a heated operating table. Catheters were placed into the left femoral artery for recording blood pressure and into the left femoral vein for compound administration. Heart rate was recorded via the lead II E.C.G. A laparotomy was performed to cannulate both ureters to prevent change of fluid volume within the bladder. A 7F cardiac catheter (with a 1.5 ml capacity balloon tip) was inserted into the bladder via the urethra. The balloon was filled with air and the catheter withdrawn until the balloon became lodged in the prostate, which was confirmed by digital pressure. Balloon pressure was recorded via a Druck transducer. Prostatic pressure and haemodynamic parameters were made on a Grass Polygraph (Grass Instruments, Quincy, Mass., U.S.A.) and the data measured on line using a Motorola 68000-based microcomputer system (Motorola Inc., Temple, Ariz., U.S.A.). Compounds were made up in PEG 300 and administered i.v. through a catheter in the femoral vein. Responses to phenylephrine (1–16 Πg/kg i.v. in saline) were obtained to generate control dose-response curves (two control curves for each experiment). Compounds were administered (in terms of compound base) at 10–300 Πg/kg i.v. 5 min before construction of phenylephrine curves (constructed up to a maximum dose of 128 Πg/kg in the presence of test compound).

Due to $\Delta_1$-related dysrhythymic properties of phenylephrine, absolute maximal responses were not obtained but were taken as 10% greater than the control response obtained with 16 Πg/kg phenylephrine. Drug concentrations were calculated on the basis of molar weight of compound/kg body weight thus allowing a "pseudo pA$_2$" calculation by Schild analysis using dose ratios derived from shifts in the phenylephrine dose-response curves.

The compounds of the invention may have the advantage that they are more potent, have a longer duration of action, have a broader range of activity, are more stable, have fewer side effects or are more selective (in particular they may have beneficial effects in benign prostatic hyperplasia without causing undesirable cardiovascular effects, for example because they are able to selectively antagonise prostatic receptor subtypes of the Al-adrenoceptor), or have other more useful properties than the compounds of the prior art.

The invention is illustrated by the following examples, in which the following abbreviations may be used:

2×m=two overlapping multiplets

DMF=dimethylformamide

DMSO=dimethylsulphoxide

EtOAc=ethyl acetate

EtOH=ethanol h=hour

MeOH=methanol min=minute n-BuOH=n-butanol

THF=tetrahydrofuran

INTERMEDIATE 1

1-(4-Morpholinecarbonyl)-1,4-diazepane Hydrochloride (a) 1-(t-Butyloxycarbonyl)-1,4-diazepane To a solution of homopiperazine (100 g, 1.0 mol) and triethylamine (210 ml, 152 g, 1.5 mol) in dichloromethane (500 ml) at 0° C. was added a solution of di-(t-butyl) dicarbonate (195 g, 0.89 mol) in dichloromethane (300 ml). The mixture was allowed to warm to room temperature and stirred for 18 hours after which time the dichloromethane was evaporated under reduced pressure. The resulting residue was partitioned between diethyl ether and 2N citric acid and the aqueous layer was extracted with diethyl ether (4×200 ml). The aqueous layer was basified with 2N aqueous sodium hydroxide and then extracted with dichloromethane (4×400 ml). The combined dichloromethane extracts were washed with water (2×), saturated brine (1×) and dried over $MgSO_4$. Evaporation under reduced pressure followed by azeotroping with dichloromethane (4×) gave the subtitle compound as a yellow waxy solid (94.3 g, 53%). $R_f$ 0.25 (0.880 aqueous ammonia:methanol:dichloromethane 1:10:90, v/v). MS m/z 201 (MH)$^+$. Found: C,58.86; H,10.03; N,13.58; $C_{10}H_{20}N_2O_2$ 0.05$CH_2Cl_2$ requires C, 59.02; H, 9.91; N,13.70%.

(b) 1-(t-Butyloxycarbonyl)-4-(4-morpholinecarbonyl)-1,4-diazepane

A solution of 1-(t-butyloxycarbonyl)-1,4-diazepane (92.0 g, 0.46 mol) and triethylamine (96.0 ml, 69.7 g, 0.69 mol) in dichloromethane (500 ml) at 0° C. was treated dropwise with a solution of 4-morpholinecarbonyl chloride (64.0 ml, 82.0 g, 0.55 mol) in dichloromethane (100 ml) and the reaction was stirred at room temperature under nitrogen for 18 hours. The reaction mixture was then diluted with dichloromethane (400 ml) and washed with 2N citric acid (3×400 ml), saturated brine (1×500 ml), dried over $MgSO_4$ and evaporated to give the subtitle compound as an off-white solid (141.7 g, 98%). $R_f$ 0.80 (0.880 aqueous ammonia:methanol:dichloromethane 1:10:90, v/v). MS m/z 314 (MH)$^+$. Found: C,57.50; H,8.69; N,13.41; $C_{15}H_{27}N_3O_4$ requires C, 57.50; H, 8.69; N,13.41%.

(c) 1-(4-Morpholinecarbonyl)-1,4-diazepane Hydrochloride.

A solution of 1-(t-butyloxycarbonyl)-4-(4-morpholinecarbonyl)-1,4-diazepane (140.0 g, 0.44 mol) in dichloromethane:methanol (1:1, v/v, 600 ml) at 0° C. was saturated with hydrogen chloride gas and the reaction mixture was stirred at room temperature under nitrogen for 18 hours after which time the reaction mixture was evaporated under reduced pressure and slurried in ethyl acetate to give, after filtration, a white hygroscopic solid. This was further purified by slurrying in acetone, filtering, washing with diethyl ether and drying in vacuo at 60° C. to give the title compound as a colourless solid (99.0 g, 90%). $R_f$ 0.41 (0.880 aqueous ammonia:methanol:dichloromethane 2:14:84, v/v). MS m/z 214 (MH)$^+$. Found: C,47.50; H,8.10; N,16.55; $C_{10}H_{19}N_3O_2$ HCl 0.2$H_2O$ requires C, 47.41; H, 8.12; N,16.59%.

INTERMEDIATE 2

1-Acetyl-4-(4-morpholinecarbonyl)-1,4-diazeyane

To a solution of 1-(4-morpholinecarbonyl)-1,4-diazepane hydrochloride (50 g, 0.2 mol) and triethylamine (42 ml, 30.5 g, 0.3 mol) in dichloromethane (400 ml) at 5° C. was added acetic anhydride (23 ml, 24.9 g, 0.24 mol) dropwise over 15 minutes and the reaction was then stirred for a further 2 hours at room temperature under nitrogen. Dilution with dichloromethane (600 ml) was followed by washing with saturated aqueous sodium bicarbonate (2×200 ml) and the combined aqueous layers extracted with dichloromethane (1×100 ml). The dichloromethane layers were combined and washed with saturated brine, dried over $MgSO_4$ and evaporated to give a light brown oil. This was dissolved in dichloromethane (300 ml) and treated with triethylamine (8 ml, 5.8 g, 0.06 mol) and ethanol (5 ml), stirred for 1 hour at room temperature then washed with saturated sodium bicarbonate and the aqueous layer extracted with dichloromethane (5×). The combined dichloromethane layers were dried over $MgSO_4$ and evaporated under reduced pressure to give a yellow oil which was then azeotroped with dichloromethane (4×) to give the title compound as a yellow oil (47.1 g, 92%). $R_f$ 0.45 (0.880 aqueous ammonia:) methanol:dichloromethane 1:10:90, v/v). MS m/z 256 (MH)$^+$. Found: C,52.62; H,8.18; N,15.02; $C_{12}H_{21}N_3O_3$ 0.3$CH_2Cl_2$ requires C, 52.61; H, 7.75; N,14.96%.

INTERMEDIATE 3

6-Acetyl-5,6,7,8-tetrahydro-1,6-naphthyridine

To a solution of 5,6,7,8-tetrahydro-1,6-naphthyridine [Shiozawa et al Chem. Pharm. Bull., 32, 2522 (1984)] (4.9 g, 0.037 mol) in dichloromethane at 0° C. was added triethylamine (6.1 ml, 0.044 mol) and acetyl chloride (3.11 ml, 0.044 mol) dropwise and the reaction was allowed to warm to room temperature and stirred for a further 18 hours. The reaction mixture was partitioned between water and dichloromethane, the layers were separated and the aqueous layer was extracted twice more with dichloromethane. The combined organic layers were dried over $MgSO_4$ and evaporated under reduced pressure to afford a residue which was purified on silica gel, eluting with 0.880 aqueous ammonia:methanol:dichloromethane (0.5:3.5:96, v/v). This afforded the title compound (58%) as an oil. $R_f$ 0.60 (0.880 aqueous ammonia:methanol:dichloromethane, 2:14:84, v/v). $^1$H NMR (CDCl$_3$): Γ=2.15 (3H, s), 3.04 (2H, m), 3.75 and 3.90 (2H, 2×m), 4.60 and 4.70 (2H, 2×s), 7.10 (1H, m), 7.42 (1H, m), 8.42 (1H, m).

INTERMEDIATE 4

2-Acetyl-5-methanesulfonamido-1,2,3,4-tetrahydroisoquinoline (a) 5-Methanesulfonamidoisoquinoline Methanesulfonyl chloride (3.2 ml, 0.042 mol) was added to a solution of 5-aminoisoquinoline (5.0 g, 0.035 mol) in pyridine (40 ml) and the mixture was allowed to stand for 72 hours. The reaction mixture was then poured into aqueous citric acid (10%, 400 ml) and extracted with ethyl acetate (2×230 ml). The organic layer was evaporated to give a residue which was purified on silica gel, eluting with dichloromethane:methanol (95:5, v/v), to afford the subtitle compound as a solid (3.55 g, 46%). $R_f$ 0.03 ($CH_2Cl_2$:diethyl ether 4:1, v/v). $^1$H NMR (D$_6$-DMSO) Γ: 3.07 (3H, s), 7.68 (1H, t), 7.75 (1H, d), 8.03 (1H, d), 8.10 (1H, d), 8.54 (1H, d), 9.32 (1H, s), 9.79 (1H, bs).

(b) 5-Methanesulfonamido-1,2,3,4-tetrahydroisoquinoline Hydrochloride

A solution of 5-methanesulfonamidoisoquinoline (3.50 g, 0.0156 mol) in ethanol (250 ml) was treated with platinum dioxide (1.5 g) and 1N aqueous hydrochloric acid (15.7 ml). The mixture was hydrogenated at a pressure of 414 kPa (60 psi) for 16 hours, after which time the reaction mixture was filtered. The filtrate was evaporated under reduced pressure and triturated with dichloromethane to afford the subtitle compound as a colourless solid. The solid residue from the filtration was taken up into methanol:water (1:2, v/v), and the suspension filtered, washing with dichloromethane (3×). This filtrate was evaporated to afford a second crop of the subtitle compound (total yield 3.45 g, 84%). $R_f$ 0.21 (0.880 aqueous ammonia:methanol:dichloromethane, 1:10:90, v/v). $^1$H NMR (D$_6$-DMSO) Γ: 2.96–3.10 (2H, m), 3.31 (3H, m), 4.21 (2H, s), 7.12 (1H, m), 7.26 (2H, m), 9.24 (1H, s), 9.61 (2H, bs).

(c) 2-Acetyl-5-methanesulfonamido-1,2,3,4-tetrahydroisoquinoline

To a solution of 5-methanesulfonamido-1,2,3,4-tetrahydroisoquinoline hydrochloride (2.87 g, 0.011 mol) in dichloromethane at 0° C. was added acetic anhydride (1.2 ml, 0.013 mol) and triethylamine (3.4 ml, 0.024 mol), and the reaction was stirred at room temperature for 16 hours. The reaction mixture was then partitioned between ethyl acetate and aqueous sodium bicarbonate solution and the aqueous phase extracted with further portions of ethyl acetate. The combined organic extracts were dried (MgSO$_4$) and evaporated to afford an oil. This was dissolved in methanol (15 ml) and treated with aqueous sodium carbonate solution (7%, w/w, 15 ml) and the mixture stirred for 16 hours at room temperature, after which time the methanol was removed under reduced pressure, the pH was adjusted to pH 8 with 2N hydrochloric acid and the product was extracted with ethyl acetate (2×). The combined organic extracts were dried (MgSO$_4$) and evaporated to give an oil which was purified on silica gel, eluting with dichloromethane:methanol (95:5, v/v) to give the title compound as an oil (2.0 g, 68%). R$_f$ 0.20 (dichloromethane:methanol 95:5, v/v). MS m/z 269 (MH)$^+$.

EXAMPLE 1

4-Amino-6-benzyloxy-7-methoxy-2-[4-(4-morpholinecarbonyl)-1,4-diazepan-1-yl]quinazoline (a) 3-Benzyloxy-4-methoxybenzonitrile 3-Benzyloxy-4-methoxybenzaldehyde (50 g, 0.21 mol) was added to a solution of sodium acetate (33.9 g, 0.41 mol) and hydroxylamine hydrochloride (28.73 g, 0.41 mol) in acetic acid (200 ml) and the resulting suspension was heated to reflux for 18 hours. After cooling, the reaction mixture was partitioned between dichloromethane and water and the aqueous phase was further extracted with dichloromethane. The combined organic layers were dried over MgSO$_4$ and evaporated to afford the subtitle compound as a buff-coloured solid (43.9 g, 89%). R$^f$ 0.70 (toluene:EtOAc 4:1, v/v).

(b) 5-Benzyloxy-4-methoxy-2-nitro-benzonitrile

A solution of 3-benzyloxy-4-methoxybenzonitrile (43.8 g, 0.18 mol) in glacial acetic acid (87 ml) was added dropwise to concentrated nitric acid (70% w/w, 244 ml) with periodic cooling to maintain the reaction temperature below 30° C. Once the addition was complete, the reaction was stirred for a further 30 minutes, after which time the mixture was poured into water (11) and stirred for 30 minutes. The resulting precipitate was isolated by filtration, washed with water and dried under reduced pressure at 50° C. to afford the subtitle compound as a white solid (35.1 g, 68%). R$_f$ 0.70 (EtOAc:hexane 1:1, v/v).

(c) 2-Amino-5-benzyloxy-4-methoxybenzonitrile

To a solution of 5-benzyloxy-4-methoxy-2-nitro-benzonitrile (35.0 g, 0.12 mol) in dichloromethane (500 ml) was added tetra-n-butylammonium chloride (20.3 g, 0.074 mol) followed by a solution of sodium dithionite hydrate (118.0 g, 0.61 mol) in H$_2$O (400 ml) and the mixture was stirred vigorously for 2 hours at room temperature. A further quantity of sodium dithionite hydrate (47.2 g) was then added and stirring continued for 1 hour. The reaction mixture was then basified with 2N aqueous sodium hydroxide and the phases separated. The aqueous layer was extracted twice more with dichloromethane and the combined organic layers dried over MgSO$_4$ and concentrated under reduced pressure to a volume of 60 ml. Treatment with excess ethereal hydrogen chloride led to the precipitation of an orange solid which was washed with diethyl ether and then dissolved in a mixture of dichloromethane and 2N aqueous sodium hydroxide. The phases were separated and the organic layer concentrated under reduced pressure and then dissolved in ethyl acetate and passed through a 5 cm plug of silica gel, eluting with ethyl acetate. On evaporation and drying under reduced pressure, the subtitle compound was obtained as a yellow solid (26.7 g, 85%). R$_f$ 0.76 (0.880 aqueous ammonia:methanol:dichloromethane 1:10:90, v/v). MS m/z 255 (MH)$^+$.

(d) 4-Amino-6-benzyloxy-2-hydroxy-7-methoxyquinazoline

A solution of 2-amino-5-benzyloxy-4-methoxybenzonitrile (26.7 g, 0.10 mol) in dichloromethane was treated with sodium cyanate (17.1 g, 0.26 mol) and then trifluoroacetic acid (20.9 ml, 0.26 mol) was added dropwise to the resulting mixture at room temperature. After 45 minutes, the mixture was diluted with dichloromethane (11) and stirred for a further 18 hours. The mixture was then concentrated under reduced pressure and partitioned between methanol and 2N aqueous sodium hydroxide and stirred for 2 hours. The methanol was then removed under reduced pressure and the yellow solid isolated by filtration, washing sequentially with water, acetone and diethyl ether to afford the subtitle compound as a yellow solid (18.0 g, 54%). A further quantity of product was obtained by concentration of the filtrate, acidification with concentrated hydrochloric acid (95 ml), warming on a steam bath for 5 minutes, cooling and neutralisation with solid potassium carbonate. The solid obtained was isolated by filtration, washing sequentially with water, ethanol and diethyl ether to afford the subtitle compound as a yellow solid (12.11 g, 93% combined yield). R$_f$ 0.23 (0.880 aqueous ammonia:methanol:dichloromethane 2:14:84, v/v). MS m/z 298 (MH)$^+$.

(e) 4-Amino-6-benzyloxy-2-chloro-7-methoxyquinazoline

N,N-Dimethyl formamide (7.9 ml, 0.10 mol) was added dropwise to phosphorus oxychloride (47.9 ml, 0.52 mol) with stirring. After 10 minutes, 4-amino-6-benzyloxy-2-hydroxy-7-methoxyquinazoline (16.4 g, 0.055 mol) was added portionwise and the resulting mixture heated at 90° C. for 1.5 hours, then cooled and poured into ethyl acetate (750 ml). The mixture was neutralised by the portionwise addition of aqueous sodium carbonate and the phases were separated. The organic layer was evaporated to dryness and the residue combined with the organic phase which was then treated with aqueous sodium hydroxide to basify (pH10) and the mixture was heated at 90° C. for 2 hours. After cooling, the mixture was partitioned between dichloromethane (11) and water (11), the organic phase washed with water, dried over MgSO$_4$ and evaporated to give a pale yellow solid. Trituration with isopropanol afforded the subtitle compound as a colourless solid (4.64 g, 27%). R$^f$ 0.64 (ethyl acetate::methanol 95:5, v/v). MS m/z 316, 318 (MH$^+$).

(f) 4-Amino-6-benzyloxy-7-methoxy-2-[4-(4-morpholinecarbonyl)-1,4-diazepan-1-yl]quinazoline 1-(4-Morpholinecarbonyl)-1,4-diazepane hydrochloride (16 g, 0.075 mol) and 4-amino-6-benzyloxy-2-chloro-7-methoxyquinazoline (15 g, 0.048 mol) were added to a solution of triethylamine (20 ml, 0.144 mol) in n-butanol (200 ml) and the reaction stirred at reflux for 1 hour. On cooling, the mixture was concentrated under reduced pressure and the residue partitioned between dichloromethane (400 ml) and water (400 ml). The phases were separated and the organic layer dried (MgSO$_4$), filtered and evaporated under reduced pressure to give a cream coloured solid. Trituration with diethyl ether gave the title compound as a solid (16.35 g, 70%). R$_f$ 0.50 (0.880 aqueous ammonia:methanol:dichloromethane 1:7:92, v/v). MS m/z 493

(MH)+. 1H-NMR (CDCl3): Γ=2.03 (2H, m), 3.18 (4H, m), 3.34 (2H, t), 3.56 (2H, m), 3.65 (5H, m), 3.85 (2H, m), 4.00 (4H, m), 5.00 (1H, bs), 5.18 (2H, s), 6.87 (1H, bs), 7.37 (4H, m), 7.47 (3H, m).

EXAMPLE 2

4-Amino-6-(4-fluorobenzyloxy)-7-methoxy-2-[4-(4-morpholinecarbonyl)-1,4-diazepan-1-yl]quinazoline Hydrochloride (a) 4-Amino-6-hydroxy-7-methoxy-2-[4-(4-morpholinecarbonyl)-1,4-diazepan-1-yl]quinazoline 10% palladium on charcoal (3 g) was added to a suspension of 4-amino-6-benzyloxy-7-methoxy-2-[4-(4-morpholinecarbonyl)-1,4-diazepan-1-yl]quinazoline (16.35 g, 0.033 mol) in ethanol (800 ml) and the reaction stirred at 50° C. under a hydrogen atmosphere of 414 kPa (60 p.s.i.) for 72 hours. On cooling, the reaction mixture was filtered through Arbocel™, washed well with further ethanol and the filtrate concentrated under reduced pressure. The crude product was purified on silica gel eluting with a solvent gradient of 0.880 aqueous ammonia:methanol:dichloromethane (0.5:3.5:96 to 1:7:92, v/v) to give the subtitle compound as a white solid (7.1 g, 53%). $R_f$ 0.17 (0.880 aqueous ammonia:methanol:dichloromethane 1:7:92, v/v). MS m/z 403 (MH)+.

(b) 4-Amino-6-(4-fluorobenzyloxy)-7-methoxy-2-[4-(4-morpholinecarbonyl)-1,4-diazepan-1-yl]quinazoline Hydrochloride A solution of 4-amino-6-hydroxy-7-methoxy-2-[4-(4-morpholinecarbonyl)-1,4-diazepan-1-yl]quinazoline (300 mg, 0.00075 mol) in dimethylformamide (3 ml) was added to a solution of sodium hydride (30 mg, 60%, 0.00075 mol) in dimethylformamide (2 ml). 4-fluorobenzyl bromide (112 Π, 0.0009 mol) was then added and the reaction stirred at room temperature for 2 hours under a nitrogen atmosphere. Water (10 ml) was added, the mixture extracted with dichloromethane (3×10 ml) and the combined organic extracts dried (MgSO4), filtered and evaporated under reduced pressure. The crude product was purified on silica gel eluting with a solvent gradient of methanol:dichloromethane (2:98 to 10:90, v/v), followed by crystallisation from ethereal hydrogen chloride to give the title compound (204 mg, 50%). $R_f$ 0.45 (0.880 aqueous ammonia:methanol:dichloromethane 1:7:92, v/v). MS m/z 511 (MH)+. 1H-NMR (CD3OD): Γ=2.04 (2H, m), 3.10 (4H, m), 3.30 (2H, m), 3.44 (2H,t), 3.60 (4H, m), 3.68 (2H, t), 3.90 (2H,t), 4.00 (5H, m), 5.16 (2H, s), 7.10 (2H, m), 7.25 (1H, s), 7.48 (2H, m), 7.66 (1H, s). Found: C, 52.44; H, 5.85; N, 13.87: $C_{26}H_{32}N_6ClFO_4$ 0.2CH2Cl2 2H2O, requires C, 52.44; H, 6.11; N, 14.01%.

EXAMPLE 3

4-Amino-6-cyclobutylmethyloxy-7-methoxy-2-[4-(4-morpholinecarbonyl)-1,4-diazepan-1-yl]quinazoline The title compound was prepared from 4-amino-6-hydroxy-7-methoxy-2-[4-(4-morpholinecarbonyl)-1,4-diazepan-1-yl]quinazoline and iodomethyl cyclobutane [Bailey et al J Org Chem, 60, 297–300 (1995)] following a similar procedure to that described in Example 2(b), and was obtained as a solid (14%). $R_f$ 0.40 (0.880 aqueous ammonia:methanol:dichloromethane 1:7:92, v/v). MS m/z 471 (MH)+. Found: C, 59.35; H, 7.12; N, 17.44; $C_{24}H_{34}N_6O_4$ 0.15CH2Cl2 0.15 H2O, requires C, 59.68; H, 7.18; N, 17.28%.

EXAMPLE 4

4-Amino-6-cyclobutyloxy-7-methoxy-2-[4-(4-morpholinecarbonyl)-1,4-diazepan-1-yl]quinazoline Hydrochloride The title compound was prepared from 4-amino-6-hydroxy-7-methoxy-2-[4-(4-morpholinecarbonyl)-1,4-diazepan-1-yl]quinazoline and cyclobutyl bromide following a similar procedure to that described in Example 2(b), allowing the reaction to stir for 12 hours at 110° C. The crude product was purified on silica gel eluting with dichloromethane:methanol:0.880 aqueous ammonia (95:5:0.5, v/v). The product was dissolved in a minimum volume of dichloromethane, triturated with ethereal hydrogen chloride, filtered and dried to give the title compound as a white solid (104 mg, 28%). MS m/z 457 (MH)+. Found: C, 52.59; H, 6.72; N, 16.13; $C_{23}H_{32}N_6O_4HCl$ 1.75H2O, requires C, 52.67; H, 7.01; N, 16.02%

EXAMPLE 5

4-Amino-6-benzyloxy-7-methoxy-2-[4-(2-tetrahydrofurancarbonyl)-1,4-diazepan-1-yl] quinazoline The title compound was prepared from 4-amino-6-benzyloxy-2-chloro-7-methoxyquinazoline and 1-(tetrahydro-2-furoyl)-piperazine hydrochloride [U.S. Pat. No. 4,026,894 (1976)] following a similar procedure to that described in Example 1(f). The crude product was purified on silica gel eluting with 0.880 aqueous ammonia:methanol:dichloromethane (1:7:92, v/v) to give the title compound as a solid (13%). $R_f$ 0.37 (0.880 aqueous ammonia:methanol:dichloromethane 1:10:90, v/v). MS m/z 464 (MH)+. 1H-NMR (CDCl3): Γ=1.92 (1H, m), 2.05 (2H, m), 2.36 (1H, m), 3.60–4.00 (12H, m), 4.66 (2H, t), 4.98 (2H, s), 5.15 (2H, s), 6.88 (1H, s), 6.93 (1H, s), 7.36 (3H, m), 7.46 (2H, m). Found: C, 62.91; H, 6.11; N, 14.61; $C_{25}H_{29}N_5O_4$ 0.2CH2Cl2, requires C, 62.99; H, 6.17; N, 14.57%.

EXAMPLE 6

4-Amino-6-benzyloxy-7-methoxy-2-[4-(4-morpholinecarbonyl)-1,4-diazepan-1-yl]quinoline Hydrochloride (a) 5-Benzyloxy-4-methoxy-2-{1-[4-(mornholinecarbonyl)-1,4-diazepan-1-yl]ethylideneamino}benzonitrile Phosphorous oxychloride (0.81 ml, 0.0086 mol) was added to a solution of 1-acetyl-4-(4-morpholinecarbonyl)-1,4-diazepane (4.02 g, 0.0157 mol) in dichloromethane (25 ml) and the mixture stirred for 30 minutes at room temperature. A solution of 2-amino-5-benzyloxy-4-methoxybenzonitnrle (2 g, 0.0078 mol) in dichloromethane (25 ml) was then added and the reaction stirred for 18 hours at 40° C. On cooling, the reaction mixture was poured carefully in to ice/water (100 ml) and extracted with dichloromethane (2×100 ml). The combined organic layers were dried (MgSO4), filtered and evaporated under reduced pressure to give a brown oil. The crude product was purified on silica gel eluting with a solvent gradient of methanol:dichloromethane (2:98 to 10:90 v/v) to give the subtitle compound. $R_f$ 0.67 (0.880 aqueous ammonia:methanol:dichloromethane 1:7:92, v/v). MS m/z 492 (MH)+.

(b) 4-Amino-6-benzyloxy-7-methoxy-2-[4-(4-morpholinecarbonyl)-1,4-diazepan-1-yl]quinoline Hydrochloride Potassium tert-butoxide (680 mg, 0.0061 mol) was added to a solution of 5-benzyloxy-4-methoxy-2-{1-[4-

(morpholinecarbonyl)-1,4-diazepan-1-yl]ethylideneamino}benzonitrile (1.5 g, 0.003 mol) in 1,2-dimethoxyethane (40 ml) and the reaction stirred at 80° C. for 2 hours. On cooling, glacial acetic acid (0.52 ml, 0.0091 mol) was added and the mixture concentrated under reduced pressure. The residue was partitioned between ethyl acetate (50 ml) and 2N aqueous sodium hydroxide solution (50 ml) and the aqueous layer further extracted with ethyl acetate (100 ml). The combined organic extracts were dried ($MgSO_4$), filtered and evaporated under reduced pressure to give a red-brown oil. The crude product was purified on silica gel eluting with a solvent gradient of methanol:dichloromethane:) 0.880 aqueous ammonia (2:98:0 to 12:84:2 v/v) followed by crystallisation from ethereal hydrogen chloride, to give the title compound as a solid (600 mg, 37%). $R_f$ 0.22 (0.880 aqueous ammonia:methanol:dichloromethane 1:7:92, v/v). MS m/z 492 $(MH)^+$. $^1$H-NMR ($CDCl_3$): Γ=2.02 (2H, q), 3.10 (4H, m), 3.30 (2H, m), 3.54 (2H, m), 3.58 (4H,m), 3.64 (2H, t), 3.95 (5H, m), 4.18 (2H, s), 5.18 (2H, s), 5.94 (1H, s), 6.90 (1H, s), 7.02 (1H, s), 7.40 (5H, m). Found: C, 56.71; H, 6.65; N. 11.87; $C_{27}H_{33}N_5O_4$ HCl $H_2O$ 0.4$CH_2Cl_2$ requires C, 56.74; H, 6.40; N, 12.07%.

EXAMPLE 7

4-Amino-6-cyclobutyloxy-7-methoxy-2-[4-(4-morpholinecarbonyl)-1,4-diazepan-1-yl]quinoline (a) 4-Amino-6-hydroxy-7-methoxy-2-[4-(4-morpholinecarbonyl)-1,4-diazepan-1-yl]quinoline 10% Palladium on charcoal (250 mg) was added to a solution of 4-amino-6-benzyloxy-7-methoxy-2-[4-(4-morpholinecarbonyl)-1,4-diazepan-1-yl]quinoline (1.01 g, 0.002 mol) in ethanol (100 ml) and the reaction stirred at room temperature under a hydrogen atmosphere of 414 kPa (60 p.s.i.) for 72 hours. The reaction mixture was filtered through Arbocel™, washing well with further ethanol. The filtrate was evaporated under reduced pressure to give the subtitle compound as a solid (770 mg, 93%). $R_f$ 0.40 (0.880 aqueous ammonia:methanol:dichloromethane 2:14:84, v/v). MS m/z 402 $(MH)^+$.

(b) 4-Amino-6-cyclobutyloxy-7-methoxy-2-[4-(4-morpholinecarbonyl)-1,4-diazepan-1-yl]quinoline 4-Amino-6-hydroxy-7-methoxy-2-[4-(4-morpholinecarbonyl)-1,4-diazepan-1-yl]quinoline (200 mg, 0.0005 mol) and cyclobutyl bromide (75 mg, 0.00055 mol) were added to a suspension of sodium hydride (20 mg, 0.0005 mol) in dimethylformamide (5 ml), and the reaction stirred under a nitrogen atmosphere at 50° C. for 18 hours. On cooling, the mixture was partitioned between ethyl acetate (15 ml) and water (15 ml), and the aqueous layer further extracted with ethyl acetate (30 ml). The combined organic extracts were dried ($MgSO_4$), filtered and evaporated under reduced pressure. The crude product was purified on silica gel eluting with a solvent gradient of 0.880 aqueous ammonia: methanol:dichloromethane (0:0:100 to 1:10:90 v/v) to give the title compound as a foam (80 mg, 35%). $R_f$ 0.65 (0.880 aqueous ammonia:methanol:dichloromethane 2:14:84, v/v). MS m/z 456 $(MH)^+$. Found: C, 56.54; H, 6.60; N, 13.83; $C_{24}H_{33}N_5O_4$ 0.6 $CH_2Cl_2$ 0.8 $H_2O$, requires C, 56.72; H, 6.93; N, 13.44%.

EXAMPLE 8

4-Amino-5-cyclobutyloxy-6,7-dimethoxy-2-[4-(4-morpholinecarbonyl)-1,4-diazepan-1-yl]quinazoline (a) Methyl 3,4-Dimethoxy-2-hydroxybenzoate A solution of diazomethane in diethyl ether (30 ml, 0.25M, 0.0075 mol) was added to a solution of 3,4-dimethoxy-2-hydroxybenzoic acid (1.5 g, 0.0075 mol) in diethyl ether (50 ml) and the reaction stirred at room temperature for 10 minutes. Glacial acetic acid was then added and stirring continued for a further 18 hours. The reaction mixture was concentrated under reduced pressure and the residue partitioned between dichloromethane (40 ml) and aqueous sodium hydrogen carbonate solution (40 ml). The aqueous phase was further extracted with dichloromethane (100 ml), the combined organic extracts dried ($MgSO_4$), filtered and evaporated under reduced pressure to give the subtitle compound as a white crystalline solid (1.5 g, 94%). $^1$H-NMR ($CDCl_3$): Γ=3.82 (9H, m), 6.48 (1H, d), 7.58 (1H, d), 10.84 (1H, s).

(b) Methyl 3,4-Dimethoxy-2-methanesulfonyloxybenzoate

Methanesulfonyl chloride (634 Π, 0.008 mol) was added dropwise to an ice-cooled solution of methyl 3,4-dimethoxy-2-hydroxybenzoate (1.58 g, 0.0075 mol) and triethylamine (1.27 ml, 0.009 mol) in dichloromethane (30 ml) and the reaction then allowed to warm to room temperature, with stirring. The reaction mixture was washed with water (2×25 ml) and the organic layer dried ($MgSO_4$), filtered and evaporated under reduced pressure. The crude product was purified on silica gel eluting with a solvent gradient of diethyl ether:hexane (60:40 to 100:0, v/v) to give the subtitle compound as a colourless oil that crystallised on standing (1.94 g, 90%). MS m/z 308 $(MNH_4)^+$.

(c) Methyl 3,4-Dimethoxy-2-methylsulfonyloxy-6-nitrobenzoate

Concentrated nitric acid (0.62 ml) was added dropwise to an ice cooled solution of methyl 3,4-dimethoxy-2-methanesulfonyloxybenzoate (1.94 g, 0.0067 mol) in acetic anhydride (3 ml) and the reaction stirred for 1 hour. Water (20 ml) was carefully added, and the resulting precipitate filtered and washed with further water. Drying under suction filtration gave the subtitle compound as a white solid (1.94 g, 86%). $^1$H-NMR ($CDCl_3$): Γ=3.34 (3H, s), 3.94 (3H, s), 4.00 (3H, s), 4.18 (3H, s), 7.68 (1H, s).

(d) Methyl 3,4-Dimethoxy-2-hydroxy-6-nitrobenzoate 4N aqueous sodium hydroxide solution (17 ml) was added to an ice cooled suspension of methyl 3,4-dimethoxy-2-methanesulfonyloxy-6-nitrobenzoate (1.74 g, 0.0052 mol) in dioxane (9 ml) and the resulting orange solution stirred for 1 hour. The reaction mixture was acidified with 2N aqueous hydrochloric acid and extracted with dichloromethane (2×50 ml). The combined organic extracts were dried ($MgSO_4$), filtered and evaporated under reduced pressure to give the subtitle compound as a white solid (1.23 g, 92%). MS m/z 275 $(MNH_4)^+$. $^1$H-NMR ($CDCl_3$): Γ=3.92 (9H, m), 6.86 (1H, s), 9.66 (1H, s).

(e) Methyl 2-Cyclobutyloxy-3,4-dimethoxy-6-nitrobenzoate

Cyclobutyl bromide (0.44 ml, 0.0047 mol) was added to a suspension of methyl 3,4-dimethoxy-2-hydroxy-6-nitrobenzoate (1 g, 0.0039 mol) and potassium carbonate (1.2 g, 0.0086 mol) in dimethylformamide (10 ml) and the reaction stirred at 100° C. for 4 hours. On cooling, aqueous sodium carbonate solution was added and the mixture extracted with ethyl acetate (2×40 ml). The combined organic extracts were washed with water, dried ($MgSO_4$), filtered and evaporated under reduced pressure. The crude product was purified on silica gel eluting with diethyl ether to give the subtitle compound as a colourless oil (511 mg, 42%). $R_f$ 0.89 (diethyl ether). MS m/z 312 $(MH)^+$. $^1$H-NMR ($CDCl_3$): Γ=1.48 (1H, m), 1.76(1H, m), 2.27 (4H, m), 2.94(9H, m), 4.70(1H, m), 7.51 (1H, s).

(f) Methyl 6-Amino-2-cyclobutyloxy-3,4-dimethoxybenzoate

A solution of sodium dithionite (3 g, 0.017 mol) in water (6 ml) was added to a solution of methyl 2-cyclobutyloxy- 3,4-dimethoxy-6-nitrobenzoate (511 mg, 0.00164 mol) and tetra-n-butylammonium chloride (280 mg, 0.001 mol) in dichloromethane (15 ml) and the reaction stirred vigorously for 1 hour at room temperature. The mixture was basified with 2N aqueous sodium hydroxide solution (10ml) and extracted with dichloromethane (3×20 ml). The combined organic extracts were washed with water (30 ml), dried ($MgSO_4$), filtered and evaporated under reduced pressure. The residue was dissolved in a minimum volume of dichloromethane and an excess of ethereal hydrogen chloride added. The resulting precipitate was filtered and partitioned between saturated aqueous sodium bicarbonate solution and dichloromethane. The organic layer was evaporated under reduced pressure to give the subtitle compound (500 mg). $R_f$ 0.70 (diethyl ether). $^1$H-NMR ($CDCl_3$): $\Gamma$=1.46 (1H, m), 1.70 (1H, m), 2.28 (4H, m), 3.72 (3H, s), 3.83 (3H, s), 3.90 (3H, s), 4.52 (1H, m), 5.20 (2H, bs), 5.82 (1H, s).

(g) 5-Cyclobutyloxy-2,4-dihydroxy-6,7-dimethoxyquinazoline

Methyl 6-amino-2-cyclobutyloxy-3,4-dimethoxybenzoate (500 mg, 0.00177 mol) was added to a solution of sodium cyanate (462 mg, 0.00708 mol) and trifluoroacetic acid (0.55 ml, 0.00708 mol) in dichloromethane (15 ml) and the reaction stirred at room temperature for 1 hour. Water (25 ml) was then added and the mixture extracted with dichloromethane (3×25 ml). The combined organic extracts were washed again with water (40 ml), dried ($MgSO_4$), filtered and evaporated under reduced pressure. The residue was suspended in a solution of sodium hydroxide (750 mg) in water (30 ml) and heated to 60° C. for 1 hour. On cooling, the mixture was acidified with concentrated hydrochloric acid, the resulting precipitate filtered and washed with water (20 ml) and diethyl ether (10 ml). Drying under air suction gave the subtitle compound as a solid (300 mg, 58%). $^1$H-NMR (DMSO-$d_6$): $\Gamma$=1.40 (1H, m), 1.67 (1H, m), 2.16 (4H, m), 3.68 (3H, s), 3.83 (3H, s), 4.58 (1H, m), 6.50 (1H, s).

(h) 5-Cyclobutyloxy-2,4-dichloro-6,7-dimethoxyquinazoline 1 drop of dimethylformamide was added to a solution of 5-cyclobutyloxy-2,4-dihydroxy-6,7-dimethoxyquinazoline (300 mg, 0.001 mol) in oxalyl chloride (1.5 ml) and the reaction stirred under a nitrogen atmosphere at 50° C. for 90 minutes. The reaction was cooled in ice, water was added and the solution basified with 2N aqueous sodium hydroxide solution. The mixture was extracted with dichloromethane (3×10 ml) and the combined organic extracts dried ($MgSO_4$), filtered and evaporated under reduced pressure to give the subtitle compound as a white solid (300 mg, 89%). $R_f$ 0.96 (diethyl ether). $^1$H-NMR ($CDCl_3$): $\Gamma$=1.52 (1H, m), 1.80 (1H, m), 2.40 (4H, m), 3.92 (3H, s), 4.02 (3H, s), 4.78 (1H, m), 7.13 (1H, s).

(i) 4-Amino-2-chloro-5-cyclobutyloxy-6,7-dimethoxyquinazoline

5-Cyclobutyloxy-2,4-dichloro-6,7-dimethoxyquinazoline (300 mg, 0.0009 mol) was suspended in a saturated ethanolic ammonia solution (10 ml) and the reaction stirred at room temperature for 1 hour. The reaction mixture was concentrated under reduced pressure, resuspended in a minimum volume of diethyl ether and the resulting solid filtered off. Drying under suction gave the subtitle compound as a white solid (189 mg, 68%). $R_f$ 0.69 (diethyl ether). $^1$H-NMR ($CDCl_3$): $\Gamma$=1.56 (1H, m), 1.82 (1H, m), 2.26 (2H, m), 2.42 (2H, m), 3.85 (3H, s), 3.94 (3H, s), 4.92 (1H, m), 5.82 (1H, bs), 6.94 (1H, s), 7.72 (1H, bs).

(j) 4-Amino-5-cyclobutyloxy-6,7-dimethoxy-2-[4-(4-morpholinecarbonyl)-1,4-diazepan-1-yl]quinazoline 4-Amino-2-chloro-5-cyclobutyloxy-6,7-dimethoxyquinazoline (184 mg, 0.00059 mol) was added to a solution of 1-(4-morpholinecarbonyl)-1,4-diazepane hydrochloride (163 mg, 0.00065mol) and triethylamine (184 $\Pi$1, 0.0013 mol) in n-butanol (6 ml) and the reaction stirred at reflux for 2 hours. On cooling, the reaction was concentrated under reduced pressure and the residue partitioned between ethyl acetate (20 ml) and water (20 ml). The aqueous layer was further extracted with ethyl acetate (2×20 ml), the combined organic extracts dried ($MgSO_4$), filtered and evaporated under reduced pressure. The crude product was purified on silica gel eluting with a solvent gradient of methanol:dichloromethane (0:100 to 7:93 v/v) to give the title compound as a white foam (110 mg, 38%). MS m/z= 487 (MH)$^+$. $^1$H-NMR ($CDCl_3$): $\Gamma$=1.53 (1H, m), 1.76 (1H, m), 2.04 (2H, m), 2.25 (2H, m), 2.38 (2H, m), 3.20 (4H, t), 3.36 (2H, t), 3.55 (2H, t), 3.66 (4H, t), 3.80 (3H, s), 3.85 (3H, m), 3.94 (6H, m), 4.86 (1H, m), 6.62 (1H, s). Found: C, 58.09; H, 6.96; N, 16.69; $C_{24}H_{34}N_6O_5$ 0.15$CH_2Cl_2$, requires C, 58.09; H, 6.92; N, 16.83%

EXAMPLE 9

4-Amino-6,7-dimethoxy-5-isopropyloxy-2-[4-(4-morpholinecarbonyl)-1,4-diazepan-1-yl]quinazoline (a) Methyl 3,4-Dimethoxy-2-isopropyloxy-6-nitrobenzoate 2-Iodopropane (0.5 ml, 0.005 mol) was added to a suspension of methyl 3,4-dimethoxy-2-hydroxy-6-nitrobenzoate (1 g, 0.0039 mol) and sodium carbonate (1.6 g, 0.015 mol) in dimethylformamide (15 ml) and the reaction stirred at 60° C. for 2 hours. On cooling, the reaction was concentrated under reduced pressure and the residue partitioned between ethyl acetate (25 ml) and water (25 ml). The aqueous layer was further extracted with ethyl acetate (2×25 ml), the combined organic extracts dried ($MgSO_4$), filtered and evaporated under reduced pressure to give the subtitle compound as a crystalline solid (1.1 g, 74%). $^1$H-NMR ($CDCl_3$): $\Gamma$=1.28 (6H, d), 3.94 (9H, m), 4.72 (1H, m), 7.49 (1H, s).

(b) Methyl 6-Amino-3,4-dimethoxy-2-isopropylbenzoate

The subtitle compound was prepared from methyl 3,4-dimethoxy-2-isopropyloxy-6-nitrobenzoate following the procedure described in Example 8(f), and was obtained as a white powder (78%). $^1$H-NMR ($CDCl_3$): $\Gamma$=1.27 (6H, d), 3.75 (3H, s), 3.82 (3H, s), 3.88 (3H, s), 4.47 (1H, m), 5.15 (2H, s), 5.94 (1H, s).

(c) 2,4-Dihydroxy-6,7-dimethoxy-5-isopropyloxyquinazoline

The subtitle compound was prepared from methyl 6-amino-3,4-dimethoxy-2-isopropyloxybenzoate following the procedure described in Example 8(g) and was obtained as a white solid (57%). MS m/z 281 (MH)$^+$. $^1$H-NMR ($CDCl_3$): $\Gamma$=1.37 (6H, d), 3.84 (3H, s), 3.94 (3H, s), 4.66 (1H, m), 6.30 (1H,s), 8.28 (1H, s), 9.70 (1H,s).

(d) 2,4-Dichloro-6,7-dimethoxy-5-isopropyloxyquinazoline

The subtitle compound was prepared from 2,4-dihydroxy-6,7-dimethoxy-5-isopropyloxyquinazoline using the procedure described in Example 8(h) and was obtained as a white solid (92%). $^1$H-NMR ($CDCl_3$): $\Gamma$=1.36 (6H, d), 3.83 (3H, s), 4.02 (3H, s), 4.82 (1H, m), 7.12 (1H, s).

(e) 4-Amino-2-chloro-6,7-dimethoxy-5-isopropyloxyquinazoline

The subtitle compound was prepared from 2,4-dichloro-6,7-dimethoxy-5-isopropyloxyquinazoline following a similar procedure to that described in Example 8(i) and was obtained as a white solid (63%). $^1$H-NMR ($CDCl_3$): $\Gamma$=1.37 (6H, d), 3.88 (3H, s), 3.86 (3H, s), 5.02 (1H, m), 5.88 (1H, bs), 6.95 (1H, s), 7.74 (1H, bs).

(f) 4-Amino-6,7-dimethoxy-5-isopropyloxy-2-[4-(4-morpholinecarbonyl)-1,4-diazepan-1-yl]quinazoline The title compound was prepared from 4-amino-2-chloro-6,7-dimethoxy-5-isopropyloxyquinazoline following the procedure described in Example 8(j). The crude product was purified on silica gel eluting with a solvent gradient of methanol:dichloromethane (0:100 to 2:98 v/v) to give the title compound as a white foam (29%). MS m/z 475 (MH)$^+$. $^1$H-NMR (CDCl$_3$): Γ=1.36 (6H, d), 2.03 (2H, m), 3.18 (4H, t), 3.38 (2H, t), 3.56 (2H, t), 3.68 (4H, t), 3.85 (6H, m), 3.94 (6H, m), 4.99 (1H, m), 6.64 (1H, s). Found: C, 56.62; H, 7.10; N, 16.75; C$_{23}$H$_{34}$N$_6$O$_5$ 0.2CH$_2$Cl$_2$, requires C, 56.69; H, 7.05; N, 17.10%.

EXAMPLE 10

4-Amino-5-cyclobutyloxy-6,7-dimethoxy-2-[4-(4-morpholinecarbonyl)-1,4-diazepan-1-yl[quinoline (a) 2-Benzyloxy-3,4-dimethoxybenzaldehyde Benzyl bromide (12.9 ml, 0.108 mol) was added to a suspension of 2-hydroxy-3,4-dimethoxybenzaldehyde (19 g, 0.104 mol) and potassium carbonate (14.41 g, 0.104 mol) in acetone (200 ml) and the reaction stirred at reflux for 3 hours. On cooling, the mixture was concentrated under reduced pressure and the residue partitioned between water (150 ml) and dichloromethane (150 ml). The organic layer was filtered through silica, washing through with hexane and then ethyl acetate. Evaporation of the filtrate under reduced pressure gave a yellow gum. The crude product was purified on silica gel eluting with ethyl acetate:hexane (30:70 v/v) to give the subtitle compound (25.9 g, 88%). R$_f$ 0.82 (ethyl acetate:hexane 1:1, v/v). MS m/z 273 (MH)$^+$.

(b) 2-Benzyloxy-3,4-dimethoxybenzonitrile

A slurry of sodium acetate (17.06 g, 0.208 mol) and hydroxylamine (14.45 g, 0.208 mol) in glacial acetic acid (120 ml) was added to 2-benzyloxy-3,4-dimethoxybenzaldehyde (28.3 g, 0.104 mol) and the resulting suspension stirred at reflux for 18 hours. On cooling, water (250 ml) was added and the mixture extracted with dichloromethane (500 ml). The combined organic extracts were dried (MgSO$_4$), filtered and evaporated under reduced pressure. The crude product was purified on silica gel eluting with hexane:ethyl acetate (80:20 v/v) to give the subtitle compound as an oil that crystallised on standing (21.06 g, 75%). R$_f$ 0.52 (ethyl acetate:hexane, 1:1, v/v). MS m/z 270 (MH)$^+$.

(c) 2-Hydroxy-3,4-dimethoxybenzonitrile

10% palladium on charcoal (2.0 g) was added to a solution of 2-benzyloxy-3,4-dimethoxybenzonitrile (20.8 g, 0.077 mol) in ethanol (250 ml) and the reaction stirred under a hydrogen atmosphere of 414 kPa (60 p.s.i.) for 4 hours. On cooling, the mixture was filtered through Arbocel™, washing with further ethanol. The filtrate was evaporated under reduced pressure to give the subtitle compound as a yellow solid (13.37 g, 97%). R$_f$ 0.19 (dichloromethane). MS m/z 197 (MNH$_4$)$^+$.

(d) 2-Cyclobutyloxy-3,4-dimethoxybenzonitrile

2-Hydroxy-3,4-dimethoxybenzonitrile (6.65 g, 0.037 mol) was added to a suspension of cyclobutyl bromide (5.01 g, 0.037 mol) and potassium carbonate (5.11 g, 0.037 mol) in dimethylformnamide (65 ml) and the reaction stirred at 80° C. for 4 hours. On cooling, the mixture was concentrated under reduced pressure and the residue partitioned between water (50 ml) and ethyl acetate (50 ml). The aqueous layer was extracted with further ethyl acetate (100 ml) and the combined organic extracts dried (MgSO$_4$), filtered and evaporated under reduced pressure to give the subtitle compound as a brown oil (6.50 g, 75%). R$_f$ 0.63 (dichloromethane). MS m/z 251 (MNH$_4$)$^+$.

(e) 2-Cyano-3-cyclobutyloxy-4,5-dimethoxynitrobenzene

Nitronium tetrafluoroborate (4.64 g, 0.035 mol) was added portionwise to an ice cooled solution of 2-cyclobutyloxy-3,4-dimethoxybenzonitrile (6.28 g, 0.027 mol) in acetonitrile (150 ml) and the reaction stirred for 1 hour. Saturated aqueous sodium bicarbonate solution (150 ml) was added and the mixture extracted with ethyl acetate (400 ml). The combined organic extracts were washed with water (150 ml), dried (MgSO$_4$), filtered and evaporated under reduced pressure to give a dark brown oil. The crude product was purified on silica gel eluting with dichloromethane to give the subtitle compound as a pale yellow solid (4.01 g, 53%). R$_f$ 0.23 (hexane:isopropyl alcohol:0.880 aqueous ammonia 90:10:0.75, v/v). MS m/z 296 (MNH$_4$)$^+$.

(f) 2-Cyano-3-cyclobutyloxy-4,5-dimethoxyaniline

A solution of sodium dithionite (27.6 g, 0.144 mol) in water (100 ml) was added to a solution of 2-cyano-3-cyclobutyloxy-4,5-dimethoxynitrobenzene (4.0 g, 0.0143 mol) and tetra-n-butylammonium chloride (2.33 g, 0.0084 mol) in dichloromethane (100 ml) and the reaction stirred vigorously for 90 minutes. 2N aqueous sodium hydroxide solution (100 ml) and dichloromethane (100 ml) were then added and stirring continued for 5 minutes. The aqueous phase was extracted with further dichloromethane (400 ml) and the combined organic extracts dried (MgSO$_4$), filtered and concentrated under reduced pressure to a volume of 50 ml. Ethereal hydrogen chloride was added and the resulting precipitate filtered and washed with diethyl ether. The solid was then partitioned between 2N aqueous sodium hydroxide (50 ml) and dichloromethane (100 ml) and the organic layer dried (MgSO$_4$), filtered and evaporated under reduced pressure to give the subtitle compound as a yellow oil (2.99 g, 86%). R$_f$ 0.75 (ethyl acetate). MS m/z 266 (MNH$_4$)$^+$.

(g) 2-Cyclobutyloxy-3,4-dimethoxy-6-{1-[4-(morpholinecarbonyl)-1,4-diazepan-1-yl] ethylideneamino}benzonitrile Phosphorous oxychloride (210 Ill, 0.0022 mol) was added to a solution of 1-acetyl-4-(4-morpholinecarbonyl)-1,4-diazepane (1.02 g, 0.0040 mol) in dichloromethane (10 ml) and the solution stirred at room temperature for 1 hour. 2-Cyano-3-cyclobutyloxy-4,5-dimethoxyaniline (500 mg, 0.002 mol) was then added and the reaction stirred at reflux under a nitrogen atmosphere for 18 hours. On cooling, water (30 ml) and aqueous sodium hydroxide solution were added and the mixture extracted with dichloromethane (2×100 ml). The combined organic extracts were dried (MgSO$_4$), filtered and evaporated under reduced pressure. The crude product was purified on silica gel eluting with dichloromethane:methanol:0.880 aqueous ammonia solution (96:3.5:0.5 v/v) to give the subtitle compound as a gum (950 mg, 97%). R$_f$ 0.62 (dichloromethane:methanol:0.880 aqueous ammonia 92:7:1, v/v). MS m/z 486 (MH)$^+$.

(h) 4-Amino-5-cyclobutyloxy-6,7-dimethoxy-2-4-(4-morpholinecarbonyl)-1,4-diazepan-1-yl]quinoline A solution of lithium diisopropylamide in tetrahydrofuran (10ml, 0.5M, 0.005 mol) was added to a solution of 2-cyclobutyloxy-3,4-dimethoxy-6-{1-[4-(morpholinecarbonyl)-1,4-diazepan-1-yl] ethylideneamino}benzonitrile (950 mg, 0.002 mol) in tetrahydrofuran (25 ml) at −70° C. and the reaction allowed to warn to room temperature under a nitrogen atmosphere. 1N aqueous citric acid solution (25 ml) was then added and the mixture extracted once with ethyl acetate (25 ml). The aqueous phase was basified using 1N aqueous sodium hydroxide solution and the mixture extracted with further ethyl acetate (60 ml) and these combined organic extracts dried (MgSO$_4$), filtered and evaporated under reduced pressure. The crude product was purified on silica gel eluting with dichloromethane:methanol:0.880 aqueous ammonia (97:3:1 v/v) and trituration with diethyl ether gave the title compound as a foam (680 mg, 67%). $R_f$ 0.31 (dichloromethane:methanol:0.880 aqueous ammonia, 97:3:1, v/v). MS m/z 486 (MH)$^+$. $^1$H-NMR (CDCl$_3$): Γ=1.45 (1H, m), 1.70 (1H, m), 2.03 (2H, m), 2.30 (4H, m), 3.30 (4H, m),3.35 (2H, m), 3.60 (8H, m), 3.80 (3H, s), 3.92 (5H, br,s), 4.80 (1H, m), 5.60 (2H, m), 5.70 (1H, s), 6.73 (1H, s). Found : C, 61.27; H, 7.39; N, 13.92; $C_{25}H_{35}N_5O_5$ 0.1$(C_2H_5)_2O_{0.3}$ $H_2O$ requires C, 61.21; H, 7.40; N, 14.05%.

EXAMPLE 11

4-Amino-5-cyclopentyloxy-6,7-dimethoxy-2-4-(4-morpholinecarbonyl)-1,4-diazepan-1-yl]quinoline (a) 2-Cyclopentyloxy-3,4-dimethoxybenzonitrile The subtitle compound was prepared from 2-hydroxy-3,4-dimethoxybenzonitrile and freshly distilled cyclopentyl bromide following the procedure described in Example 10(d). The crude product was purified on silica gel eluting with dichloromethane to give the subtitle compound as a colourless oil (95%). $R_f$ 0.50 (dichloromethane). MS m/z 265 (MNH$_4$)$^+$.

(b) 2-Cyano-3-cyclopentyloxy-4,5-dimethoxynitrobenzene

The subtitle compound was prepared from 2-cyclopentyloxy-3,4-dimethoxybenzonitrile following the procedure described in Example 10(e) and was obtained as a pale yellow oil (43%). $R_f$ 0.35 (hexane:isopropyl alcohol:0.880 aqueous ammonia 90:10:0.75, v/v). MS m/z 310 (MNH$_4$)$^+$.

(c) 2-Cyano-3-cyclopentyloxy-4,5-dimethoxyaniline

The subtitle compound was prepared from 2-cyano-3-cyclopentyloxy-4,5-dimethoxynitrobenzene following the procedure described in Example 10(f) and was obtained as a cream coloured solid (66%). $R_f$ 0.79 (dichloromethane:methanol:0.880 aqueous ammonia, 92:7:1, v/v). $^1$H-NMR (CDCl$_3$): Γ=1.57 (2H, m), 1.70 (2H, m), 1.90 (4H, m), 3.68 (3H, s), 3.82 (3H, s), 5.10 (1H, m), 5.98 (1H, s).

(d) 2-Cyclopentyloxy-3,4-dimethoxy-5-{1-[4-(morpholinecarbonyl)-1,4-diazepan-1-yl]ethylideneamino}benzonitrile The subtitle compound was prepared from 2-cyano-3-cyclopentyloxy-4,5-dimethoxyaniline following the procedure described in Example 10(g). The crude product was purified on silica gel eluting with methanol:dichloromethane (3:97 v/v) to give the subtitle compound as an orange oil (98%). $R_f$ 0.27 (dichloromethane:methanol 95:5, v/v). MS m/z 500 (MH)$^+$.

(e) 4-Amino-5-cyclopentyloxy-6,7-dimethoxy-2-[4-(4-morpholinecarbonyl)-1,4-diazepan-1-yl]quinoline The title compound was prepared from 2-cyclopentyloxy-3,4-dimethoxy-6-{1-[4-(morpholinecarbonyl)-1,4-diazepan-1-yl]ethylideneamino}benzonitrile following a similar procedure to that described in Example10(h). The crude product was purified on silica gel eluting with a solvent gradient of dichloromethane:methanol:0.880 aqueous ammonia (96:3.5:0.5 to 92:7:1, v/v) to give the title compound as a white foam (14%). $R_f$ 0.31 (dichloromethane:methanol:0.880 aqueous ammonia, 97:2:1, v/v). MS m/z 500 (MH)$^+$. $^1$H-NMR (CDCl$_3$): Γ=1.60 (2H, m), 1.70–1.95 (6H, m), 2.05 (2H, m), 3.15 (4H, t), 3.35 (2H, t), 3.50–3.75 (8H, m), 3.85 (3H, s), 3.95 (5H, m), 5.22 (1H, m), 5.58 (2H, bs), 5.70 (1H, s), 6.75 (1H, s).

EXAMPLE 12

4-Amino-5-cyclobutyloxy-6,7-dimethoxy-2-(5,6,7,8-tetrahydro-1,6-naphthyridin-6-yl)quinoline Hydrochloride (a) 2-Cyclobutyloxy-3,4-dimethoxy-6-[1-(5,6,7,8-tetrahydro-1,6-naphthyridin-6-yl)ethylideneamino]benzonitrile The subtitle compound was prepared from 2-cyano-3-cyclobutyloxy-4,5-dimethoxyaniline and 6-acetyl-5,6,7,8-tetrahydro-1,6-naphthyridine following the procedure described in Example 10(g), allowing the reaction to reflux for 3 hours. The crude product was purified on silica gel eluting with ethyl acetate:methanol:0.880 aqueous ammonia solution (95:5:1, v/v) to give the subtitle compound as a gum (382 mg, 48%). $R_f$ 0.53 (dichloromethane: methanol:0.880 aqueous ammonia 90:10:1, v/v). MS m/z 407 (MH)$^+$.

(b) 4-Amino-5-cyclobutyloxy-6,7-dimethoxy-2-(5,6,7,8-tetrahydro-1,6-naphthyridin-6-yl)quinoline Hydrochloride The title compound was prepared from 2-cyclobutyloxy-3,4-dimethoxy-6-[1-(5,6,7,8-tetrahydro-1,6-naphthyridin-6-yl)ethylideneamino]benzonitrile following a similar procedure to that described in Example 10(h). The crude product was purified on silica gel eluting with dichloromethane:methanol:0.880 aqueous ammonia (96:3.5:0.5 v/v) followed by suspension in ethereal hydrogen chloride to give the title compound as a sand-coloured solid (18%). MS m/z 407 (MH)$^+$. $^1$H-NMR (DMSO-d$_6$): Γ=1.45 (1H, m), 1.66 (1H, m), 2.23 (4H, m), 3.30 (2H, m), 3.70 (3H, s), 3.84 (3H, s), 4.04 (2H, m), 4.78 (1H, m), 4.95 (2H, s), 6.18 (1H, s), 7.64 (1H, s), 7.75 (2H, m), 8.10 (1H, bs), 8.18 (1H, m), 8.64 (1H, s), 12.47 (1H, s). Found: C, 55.32; H, 6.29; N, 10.56; $C_{23}H_{26}N_4O_3$·HCl 1.5$H_2O$ 0.5$CH_2Cl_2$, requires C, 55.08; H, 6.10; N, 10.93%.

EXAMPLE 13

4-Amino-5-cyclopentyloxy-6,7-dimethoxy-2-(5,6,7,8-tetrahydro-1,6-naphyridin-6-yl)quinoline (a) 2-Cyclopentyloxy-3,4-dimethoxy-6-[1-(5,6,7,8-tetrahydro-1,6-naphyridin-6-yl)ethylideneamino]benzonitrile The subtitle compound was prepared from 2-cyano-3-cyclopentyloxy-4,5-dimethoxyaniline and 6-acetyl-5,6,7,8-tetrahydro-1,6-naphthyridine following the procedure described in Example 10(g). The crude product was purified on silica gel eluting with methanol:dichloromethane (2:98 v/v) to give the subtitle compound as a colourless oil (57%). $R_f$ 0.51 (dichloromethane:methanol:0.880 aqueous ammonia, 92:7:1, v/v). MS m/z 421 (MH)$^+$. $^1$H-NMR (CDCl$_3$): Γ=1.60–2.00 (8H, m), 3.10 (2H, t), 3.83 (3H, s), 3.95 (5H, m), 4.86 (2H, s), 5.22 (1H, m), 5.78 (2H, bs), 5.90 (1H, s), 7.03 (1H, bs), 7.12 (1H, dd), 7.50 (1H, d), 8.42 (1H, d).

(b) 4-Amino-5-cyclopentyloxy-6,7-dimethoxy-2-(5 6,7,8-tetrahydro-1,6-naphyridin-6-yl)quinoline The title compound was prepared from 2-cyclopentyloxy-3,4-dimethoxy-6-[1-(5,6,7,8-tetrahydro-1,6-naphyridin-6-yl)ethylideneamino]benzonitrile following a similar procedure to that described in Example 10(h). The crude product was purified on silica gel eluting with dichloromethane:methanol (95:5 v/v) to give the title compound as a gum (5%). MS m/z 421 (MH)$^+$.

EXAMPLE 14

4-Amino-7-methoxy-2-[4-(4-morpholinecarbonyl)-1,4-diazepan-1-yl]5-(2,2,2-trifluoroethoxy)quinoline Hydrochloride (a) 4-Cyano-3-fluoro-5-(2,2,2-trifluoroethoxy)anisole Sodium hydride (1.6 g, 60%, 0.040 mol) was added to a solution of trifluoroethanol (4.0 g, 0.040 mol) in dimethylformamide (50 ml) and the solution stirred for 90 minutes. This solution was then added to 4-cyano-3,5-difluoroanisole [Grey et al, Mol Cryst Liq Cryst, 172, 165–189 (1989)] (6.30 g, 0.037 mol) in tetrahydrofuran (50 ml) and the reaction stirred at room temperature for 2 hours. The reaction mixture was poured into diethyl ether (250 ml) washed with water (2×150 ml) and then brine (50 ml). The organic layer was dried (MgSO$_4$), filtered and evaporated under reduced pressure, then triturated with diethyl ether:hexane to give the subtitle compound as white crystals (5.92 g, 59%). R$_f$ 0.14 (dichloromethane:hexane, 1:2, v/v). MS m/z 267 (MNH$_4$)$^+$.

(b) 3-Azido-4-cyano-5-(2,2,2-trifluoroethoxy)anisole

Sodium azide (1.77 g, 0.027 mol) was added to a solution of 4-cyano-3-fluoro-5-(2,2,2-trifluoroethoxy)anisole (5.66 g, 0.0227 mol) in dimethylformamide and the reaction stirred under a nitrogen atmosphere at 115° C. for 2 hours. On cooling, the reaction mixture was poured into diethyl ether (400 ml), washed with water (2×100 ml) and then brine (50 ml). The organic phase was dried (MgSO$_4$), filtered and evaporated under reduced pressure to give an off-white foam (5.66 g, 91%). R$_f$ 0.10 (dichloromethane:hexane, 1:2, v/v). MS m/z 273 (MH)$^+$.

(c) 3-Amino-4-cyano-5-(2,2,2-trifluoroethoxy)anisole

3-Azido-4-cyano-5-(2,2,2-trifluoroethoxy)anisole (5.66 g, 0.0208 mol) was added to a suspension of magnesium turnings (1.86 g, 0.0775 mol) in methanol (150 ml) and the reaction stirred at room temperature for 40 hours. The reaction was concentrated under reduced pressure to a minimum volume and ethyl acetate (200 ml) added. The mixture was washed with saturated aqueous ammonium chloride solution (75 ml) and brine (75 ml) and then dried (MgSO$_4$), filtered and evaporated under reduced pressure. Trituration with diethyl ether:hexane gave the subtitle compound as a brown solid (4.51 g, 88%). R$_f$ 0.46 (ethyl acetate:hexane, 1:1, v/v). MS m/z 247 (MH)$^+$.

(d) 2-(2,2,2-Trifluoroethoxy)-4-methoxy-6-{1-[4-(morpholinecarbonyl)-1,4-diazepan-1-yl]ethylideneamino}benzonitrile The subtitle compound was prepared from 3-amino-4-cyano-5-(2,2,2-trifluoroethoxy)-anisole and 1-acetyl-4-(4-morpholinecarbonyl)-1,4-diazepane following a similar procedure to that described in Example 10(g) allowing the reaction to stir for 60 hours at room temperature. The crude product was purified on silica gel eluting with a solvent gradient of dichloromethane:methanol (100:0 to 95:5, v/v). The product was dissolved in a minimum volume of dichloromethane and an excess of ethereal hydrogen chloride added. The resulting precipitate was filtered off and partitioned between saturated aqueous sodium hydroxide solution (100 ml ) and dichloromethane (200 ml). The organic layer was dried (MgSO$_4$) and evaporated under reduced pressure to give the subtitle compound (1.83 g, 95%). R$_f$ 0.58 (dichloromethane:methanol:0.880 aqueous ammonia 92:7:1, v/v). MS m/z 484 (MH)$^+$.

(e) 4-Amino-7-methoxy-2-[4-(4-morpholinecarbonyl)-1,4-diazepan-1-yl]-5-(2,2,2-trifluoroethoxy)quinoline Hydrochloride Zinc chloride (3.0 g, 0.022 mol) was added to a solution of 4-methoxy-2-{1-[4-(morpholinecarbonyl)-1,4-diazepan-1-yl]ethylideneamino}-6-(2,2,2-trifluoroethoxy)-benzonitrile (900 mg, 0.00186 mol) in tetrahydrofuran (50 ml) and the mixture concentrated under reduced pressure. The residue was then heated at 190° C. under vacuum for 30 minutes. On cooling, the residue was dissolved in ethyl acetate (100 ml ), ethylenediaminetetraacetic acid disodium salt (10 g, 0.027 mol) was added and the mixture basified with 2N aqueous sodium hydroxide solution. The organic phase was separated, washed with brine (50 ml), dried (MgSO$_4$), filtered and evaporated under reduced pressure. The crude product was purified on silica gel eluting with a solvent gradient of dichloromethane:methanol:0.880 aqueous ammonia (100:0:0 to 93:7:1, v/v), followed by crystallisation from acetone/ethereal hydrogen chloride to give the title compound as a solid (66 mg, 7%). MS m/z 484 (MH)$^+$. $^1$H-NMR (CDCl$_3$): Γ=2.07 (2H, m), 3.04 (4H, m), 3.26 (2H, t), 3.52 (4H, m), 3.60 (2H, t), 3.78 (2H, t), 3.88 (3H, s), 4.09 (2H, q), 5.73 (1H, s), 6.19 (1H, s), 6.80 (2H, bs), 8.38 (1H, s), 12.4 (1H, s). Found: C, 47.02; H, 5.93; N, 12.41; C$_{22}$H$_{28}$F$_3$N$_5$O$_4$HCl, requires C, 47.02; H, 5.57; N, 12.08%.

EXAMPLE 15

4-Amino-5-cyclobutyloxy-7-methoxy-2-[4-(4-morpholinecarbonyl)-1,4-diazepan-1-yl]quinoline (a) 4-Cyano-3-fluoro-5-cyclobutyloxyanisole The subtitle compound was prepared from 4-cyano-3,5-difluoroanisole and cyclobutanol following the procedure described in Example 14(a). The crude product was purified on silica gel eluting with dichloromethane:hexane (60:40 v/v) to give the subtitle compound as a white solid (92%). R$_f$ 0.26 (dichloromethane:hexane 1:2, v/v). MS m/z 239 (MNH$_4$)$^+$.

(b) 3-Azido-4-cyano-5-cyclobutyloxyanisole

The subtitle compound was prepared from the product of step (a) following the procedure described in Example 14(b). The crude product was purified on silica gel eluting with dichloromethane:hexane (60:40 v/v) to give the subtitle compound as a colourless oil that crystallised on standing (1.33 g, 54%). R$_f$ 0.29 (dichloromethane:hexane 1:1, v/v). MS m/z 262 (MNH$_4$)$^+$.

(c) N-(2-Cyano-3-cyclobutyloxy-5-methoxy)-P,P,P-triphenylphosphine Imide

Triphenylphosphine (1.42 g, 0.0054 mol) was added to a solution of 3-azido-4-cyano-5-cyclobutyloxyanisole (1.32 g, 0.0054 mol) in tetrahydrofuran (20 ml) and the solution stirred at room temperature for 1 hour. Water (1 ml) was added and the reaction stirred for a further 18 hours and the reaction then concentrated under reduced pressure. The crude product was purified on silica gel eluting with a solvent gradient of dichloromethane: methanol (100:0 to 97:3 v/v) to give the subtitle compound as a white solid (2.17 g, 84%). R$_f$ 0.07 (dichloromethane). MS m/z 479 (MH)$^+$.

(d) 3-Amino-4-cyano-5-cyclobutyloxyanisole

N-(2-Cyano-3-cyclobutyloxy-5-methoxy)-P,P,P-triphenylphosphine imide (2.17 g, 0.00453 mol) was added to a solution of 2N aqueous hydrochloric acid (5 ml), water (50 ml), methanol (50 ml) and dichloromethane (50 ml) and the reaction stirred at reflux for 16 hours. On cooling, the mixture was concentrated under reduced pressure and the residue partitioned between ethyl acetate (100 ml ) and 0.5N aqueous sodium hydroxide (50 ml). The phases were separated and the organic, washed with brine (50 ml), dried (MgSO$_4$), filtered and evaporated under reduced pressure. The crude product was purified on silica gel eluting with a solvent gradient of dichloromethane:methanol (100:0 to 98:2 v/v) to give the subtitle compound as a white solid (866 mg, 88%). R$_f$ 0.64 (ethyl acetate:hexane, 1:1, v/v). MS m/z 219 (MH)$^+$.

(e) 2-Cyclobutyloxy-4-methoxy-6-{1-[4-(morpholinecarbonyl)-1,4-diazepan-1-yl]ethylideneamino}benzonitrile The subtitle compound was prepared from 3-amino-4-cyano-5-cyclobutyloxyanisole and 1-acetyl-4-(4-morpholinecarbonyl)-1,4-diazepane following the procedure described in Example 14(d) (93%). R$_f$ 0.52 (dichloromethane:methanol:0.880 aqueous ammonia, 92:7:1, v/v). MS m/z 456 (MH)$^+$.

(f) 4-Amino-5-cyclobutyloxy-7-methoxy-2-[4-(4-morpholinecarbonyl)-1,4-diazepan-1-yl]quinoline Potassium tert-butoxide (810 mg, 0.00725 mol) was added to a solution of 2-cyclobutyloxy-4-methoxy-6-{1-[4-(morpholinecarbonyl)-1,4-diazepan-1-yl]ethylideneamino}benzonitrile (1.65 g, 0.00363 mol) in 1,2-dimethoxyethane (250 ml) and the reaction stirred at 90° C. under a nitrogen atmosphere for 1 hour. On cooling, the reaction mixture was washed with 1N aqueous citric acid solution (100 ml) and extracted with ethyl acetate (100 ml). The aqueous layer was then basified with 2N aqueous sodium hydroxide solution and extracted with dichloromethane (2×100 ml). These combined organic extracts were dried (MgSO$_4$), filtered and evaporated under reduced pressure. The crude product was purified on silica gel eluting with a solvent gradient of dichloromethane:methanol:0.880 aqueous ammonia (100:0:0 to 91:9:1 v/v) gave the title compound as a foam (0.93 g, 56%). R$_f$ 0.27 (dichloromethane:methanol:0.880 aqueous ammonia, 97:2:1, v/v). MS m/z 456 (MH)$^+$. $^1$H-NMR (CDCl$_3$): Γ=1.75 (1H, m), 1.92 (1H, m), 2.05 (2H, m), 2.24 (2H, m), 2.54 (2H, m), 3.14 (4H, t), 3.34 (2H, t), 3.57 (2H, t), 3.64 (4H, t), 3.70 (2H, t), 3.88 (3H, s), 3.94 (2H, bm), 4.62 (1H, m), 5.55 (1H, bs), 5.70 (1H, s) 5.96 (1H, s), 6.56 (1H, bs). Found: C, 60.87; H, 7.45; N, 14.79; C$_{24}$H$_{33}$N$_5$O$_4$ H$_2$O, requires C, 60.67; H, 7.08; N, 14.51%.

EXAMPLE 16

4-Amino-6,7-dimethoxy-5-(2,2,2-trifluoroethoxy)-2-[4-(4-morpholinecarbonyl)-1,4-diazepan-1-yl]quinoline (a) 3,4-Dimethoxy-2-(2,2,2,-trifluoroethoxy)benzonitrile Potassium carbonate (6.91 g, 0.05 mol) was added to a stirred solution of 2-hydroxy-3,4-dimethoxybenzonitrile (from Example 10(c), 5.61 g, 0.031 mol) in dimethylformamide (30 ml). This was followed by the addition of a solution of 2,2,2-trifluoroethyl triflate (23.2 g, 0.10 mol). in dichloromethane (100 ml ) and the reaction was stirred at room temperature for 18 hours. The reaction was partitioned between 2N hydrochloric acid and ethyl acetate, the organic layer separated, washed sequentially with saturated aqueous brine and water, dried (MgSO$_4$) and evaporated under reduced pressure. Trituration with diethyl ether followed by filtration afforded the subtitle compound as a colourless solid (7.67 g, 94%). R$_f$ 0.76 (dichloromethane:methanol 95:5, v/v). MS m/z 279 (MNH$_4$)$^+$.

(b) 2-Cyano-4,5-dimethoxy-3-(2,2,2-trifluoroethoxy)nitrobenzene

Ammonium nitrate (2.82 g, 0.035 mol) and trifluoroacetic anhydride (12.4 ml, 0.088 mol) were added to a solution of 3,4-dimethoxy-2-(2,2,2,-trifluorethoxy)benzonitrile in dichloromethane. The temperature was maintained between 20° C. and 30° C. for 2 hours, after which time the reaction mixture was washed with saturated aqueous sodium bicarbonate solution. The organic layer was separated, dried (MgSO$_4$) and evaporated under reduced pressure. Trituration with diethyl ether followed by filtration afforded a first crop of product. The filtrate was purified on silica gel, eluting with dichloromethane to afford the subtitle compound as a colourless solid (combined yield 6.56 g, 73%). R$_f$ 0.31 (ethyl acetate:hexane 20:80, v/v). MS m/z 324 (MNH$_4$)$^+$.

(c) 2-Cyano-4,5-dimethoxy-3-(2,2,2-trifluoroethoxy)aniline

The subtitle compound was prepared from 2-cyano-4,5-dimethoxy-3-(2,2,2-trifluoroethoxy)nitrobenzene using Na$_2$S$_2$O$_4$ following the procedure described in Example 10(f) (87%). R$_f$ 0.27 (dichloromethane). MS m/z 294 (MNH$_4$)$^+$.

(d) 3,4-Dimethoxy-6-{1-[4-(morpholinecarbonyl)-1,4-diazepan-1-yl]ethylideneamino}-2-(2,2,2-trifluoroethoxy)benzonitrile The subtitle compound was prepared from 2-cyano-4,5-dimethoxy-3-(2,2,2-trifluoroethoxy)aniline and 1-acetyl-4-(4-morpholinecarbonyl)-1,4-diazepane following the procedure described in Example 10(g) (73%). R$_f$ 0.16 (dichloromethane:methanol 95:5, v/v). MS m/z 514 (MH)$^+$.

(e) 4-Amino-6,7-dimethoxy-5-(2,2,2-trifluoroethoxy)-2-[4-(4-morpholinecarbonyl)-1,4-diazepan-1-yl]quinoline The title compound was prepared from 3,4-dimethoxy-6-{1-[4-(morpholinecarbonyl)-1,4-diazepan-1-yl]ethylideneamino}-2-(2,2,2-trifluoroethoxy)benzonitrile following the method of Example 14(e). Purification on silica gel, eluting with dichloromethane: methanol (95:5, v/v) afforded the title compound as a colourless foam (7%). R$_f$ 0.25 (dichloromethane:methanol:0.880 aqueous ammonia, 90:10:1, v/v). MS m/z 514 (MH)$^+$. $^1$H-NMR (CDCl$_3$): Γ=2.05 (2H, m), 3.15 (4H, t), 3.34 (2H, t), 3.58 (2H, m), 3.64 (4H, t), 3.70 (2H, m), 3.86 (3H, s), 3.95 (5H, m), 4.60 (2H, q), 5.37 (2H, bs), 5.78 (1H, s),6.83 (1H, bs).

EXAMPLE 17

4-Amino-5-cyclobutyloxy-6,7-methoxy-2-(5-methanesulfonamido-1,2,3,4-tetrahydroisoquinol-2-yl)quinoline (a) 6-Cyclobutyloxy-3,4-dimethoxy-[1-(5-methanesulfonamido-1,2,3,4-tetrahydroisoquinol-2-yl)ethylideneamino]benzonitrile The subtitle compound was prepared from 2-cyano-3-cyclobutyloxy-4,5-dimethoxyaniline and 2-acetyl-5-methanesulfonamido-1,2,3,4-tetrahydroisoquinoline following the procedure described in Example 10(g). Trituration with diethyl ether afforded the subtitle compound as a colourless solid (85%). R$_f$ 0.14 (ethyl acetate:hexane 1:1, v/v).

(b) 4-Amino-5-cyclobutyloxy-6,7-methoxy-2-(5-methanesulfonamido-1,2,3,4-tetrahydroisoquinol-2-yl)quinoline The title compound was prepared from 6-cyclobutyloxy-3,4-dimethoxy-[1-(5-methanesulfonamido-1,2,3,4-tetrahydroisoquinol-2-yl)ethylideneamino]benzonitrile following the procedure described in Example 15(f). The title compound was obtained as a light brown foam (100%). R$_f$ 0.09 (ethyl acetate). $^1$H-NMR (CDCl$_3$): Γ=1.50 (1H, m), 1.76 (1H, m), 2.15–2.40 (3H, m), 2.87 (2H, m), 3.00 (3H, s), 3.81 (3H, s), 3.88 (2H, m), 3.97 (3H, s), 4.78 (2H, s,), 4.81 (1H, m), 5.78 (2H, bs), 5.88 (1H, s), 6.92 (2H, s), 7.10 (1H, s), 7.21 (1H, t), 7.28 (2H, m).

EXAMPLE 18

The compound of Example 3 was tested in the first screen described above ("Contractile responses of human prostate") and found to have a pA$_2$ value of 9.2.

What is claimed is:

1. A compound of formula I,

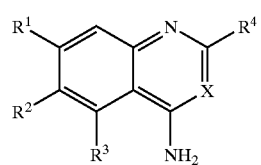

I wherein
- $R^1$ is $C_{1-4}$ alkoxy optionally substituted by one or more fluorine atoms;
- each of $R^2$ and $R^3$ is, independently, H, $C_{1-6}$ alkoxy (optionally substituted by one or more fluorine atoms, or by phenyl which may in turn be substituted by one or more fluorine atoms), or cyclobutyloxy;
- $R^4$ is a piperidine ring which piperidine ring is fused to a pyridine ring or to a benzene ring, the ring system as a whole being substituted by $NHSO_2(C_{1-4}$ alkyl);
- X is CH or N;
- provided that $R^2$ and $R^3$ are not both H;
- and provided that when X represents N, then $R^4$ is not naphthyridine;

or a pharmaceutically acceptable salt thereof.

2. A compound according to claim 1, wherein $R^1$ represents methoxy.

3. A compound according to claim 1, wherein $R^2$ represents H or methoxy.

4. A compound according to claim 1, wherein $R^3$ represents cyclobutyloxy or $CF_3CH_2O$.

5. A compound according to claim 1 for use as a pharmaceutical.

6. A pharmaceutical formulation including a compound according to claim 1 in admixture with a pharmaceutically acceptable adjuvant, diluent or carrier.

7. A method of treatment of benign prostatic hyperplasia, which comprises administration of a compound according to claim 1 to a patient in need of such treatment.

* * * * *